US00PP36244P2

(12) United States Plant Patent
Philley

(10) Patent No.: US PP36,244 P2
(45) Date of Patent: Nov. 5, 2024

(54) BERMUDAGRASS PLANT NAMED 'MSB-1017'

(50) Latin Name: ***Cynodon dactylon* x *Cynodon transvaalensis***
Varietal Denomination: MSB-1017

(71) Applicant: Mississippi State University, Starkville, MS (US)

(72) Inventor: H. Wayne Philley, Mathiston, MS (US)

(73) Assignee: Mississippi State University, Starkville, MS (US)

( * ) Notice: Subject to any disclaimer, the term of this patent is extended or adjusted under 35 U.S.C. 154(b) by 0 days.

(21) Appl. No.: 18/370,647

(22) Filed: Sep. 20, 2023

(51) Int. Cl.
*A01H 5/12* (2018.01)
*A01H 6/46* (2018.01)

(52) U.S. Cl.
USPC ..... Plt./389

(58) Field of Classification Search
USPC ..... Plt./384, 388, 389
See application file for complete search history.

(56) References Cited

U.S. PATENT DOCUMENTS

PP9,888 P * 5/1997 Brown ..... Plt./389
PP35,548 P2 * 12/2023 Wu ..... Plt./389

* cited by examiner

*Primary Examiner* — Karen M Redden
(74) *Attorney, Agent, or Firm* — Weatherly IP Solutions, LLC; James M. Weatherly

(57) ABSTRACT

A new *Bermudagrass* plant particularly distinguished by having a fine leaf texture, a dark green genetic color, reduced seedhead production, fast establishment, high density, and disease resistance leafspot (*Bipolaris cynodontis*), is disclosed.

7 Drawing Sheets

Genus and species: *Cynodon dactylon x Cynodon transvaalensis.*

Variety denomination: 'MSB-1017'.

BACKGROUND OF THE NEW PLANT

Bermudagrass 'MSB-1017' is a new and distinct bermudagrass cultivar. The female parent is 'Riley's Super Sport' with the commercial name Celebration (U.S. Plant Pat. No. 11,131), a tetraploid (2n=4x=36) common bermudagrass (*C. dactylon*) cultivar; the male parent is an African bermudagrass (*C. transvaalensis*) named 'trans1' (2n=2x=18). Accordingly, 'MSB-1017' is a triploid (2n=3x=27) and does not produce viable seed. Cross pollination was performed in summer 2015 in Starkville, Mississippi. Seeds from the cross were germinated in February 2016 in a controlled-temperature chamber. The seedlings were then individually transplanted to a greenhouse. 'MSB-1017' has been vegetatively propagated since germination. 'MSB-1017' was found to reproduce true to type in successive generations of asexual propagation via vegetative cuttings in Starkville, Mississippi.

SUMMARY

The following are the most outstanding and distinguishing characteristics of this new variety when grown under normal horticultural practices in Starkville, Mississippi.

1. 'MSB-1017' is characterized with fine leaf texture;
2. 'MSB-1017' is characterized by a dark green color;
3. 'MSB-1017' is characterized by reduced seedhead production;
4. 'MSB-1017' is characterized by fast establishment;
5. 'MSB-1017' is characterized by high density; and 6. 'MSB-1017' is characterized by disease resistance leafspot (*Bipolaris cynodontis*).

DESCRIPTION OF THE PHOTOGRAPHS

This new Bermudagrass plant 'MSB-1017' is illustrated by the accompanying photographs. The colors shown are as true as can be reasonably obtained by conventional photographic procedures.

Figure 1:
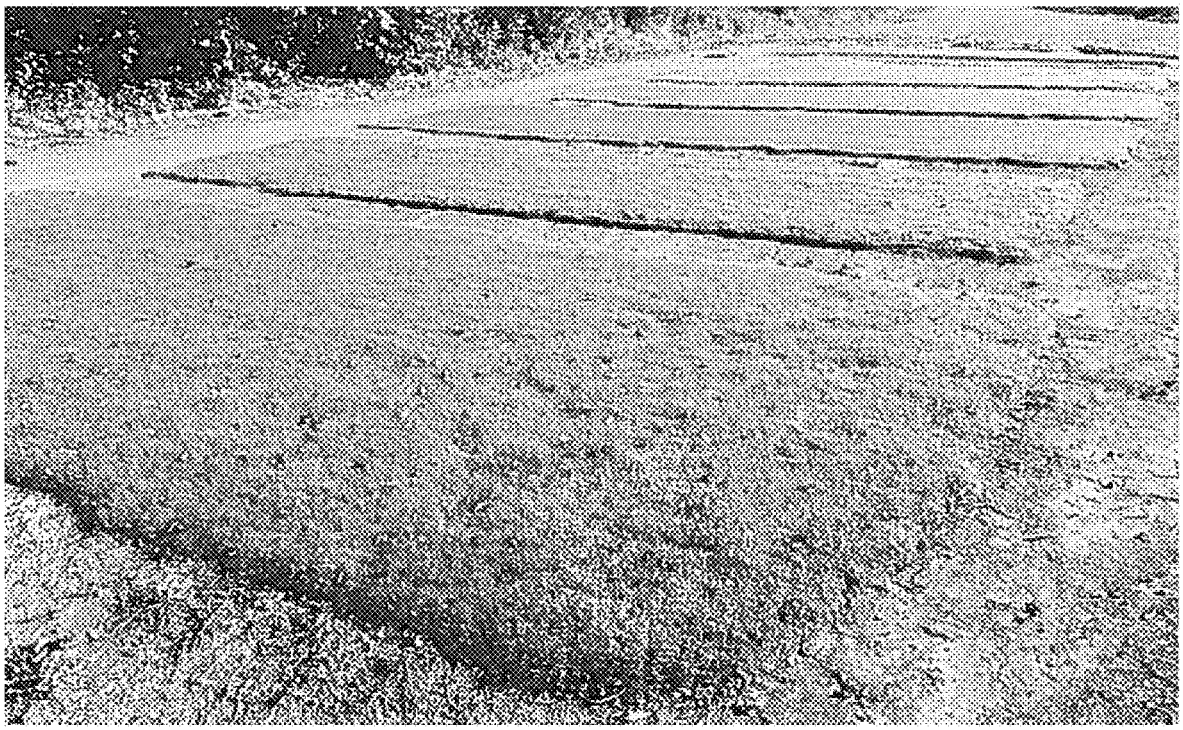

FIG. 1. Photo of 'MSB-1017' plot in South Carolina.

Figure 2:
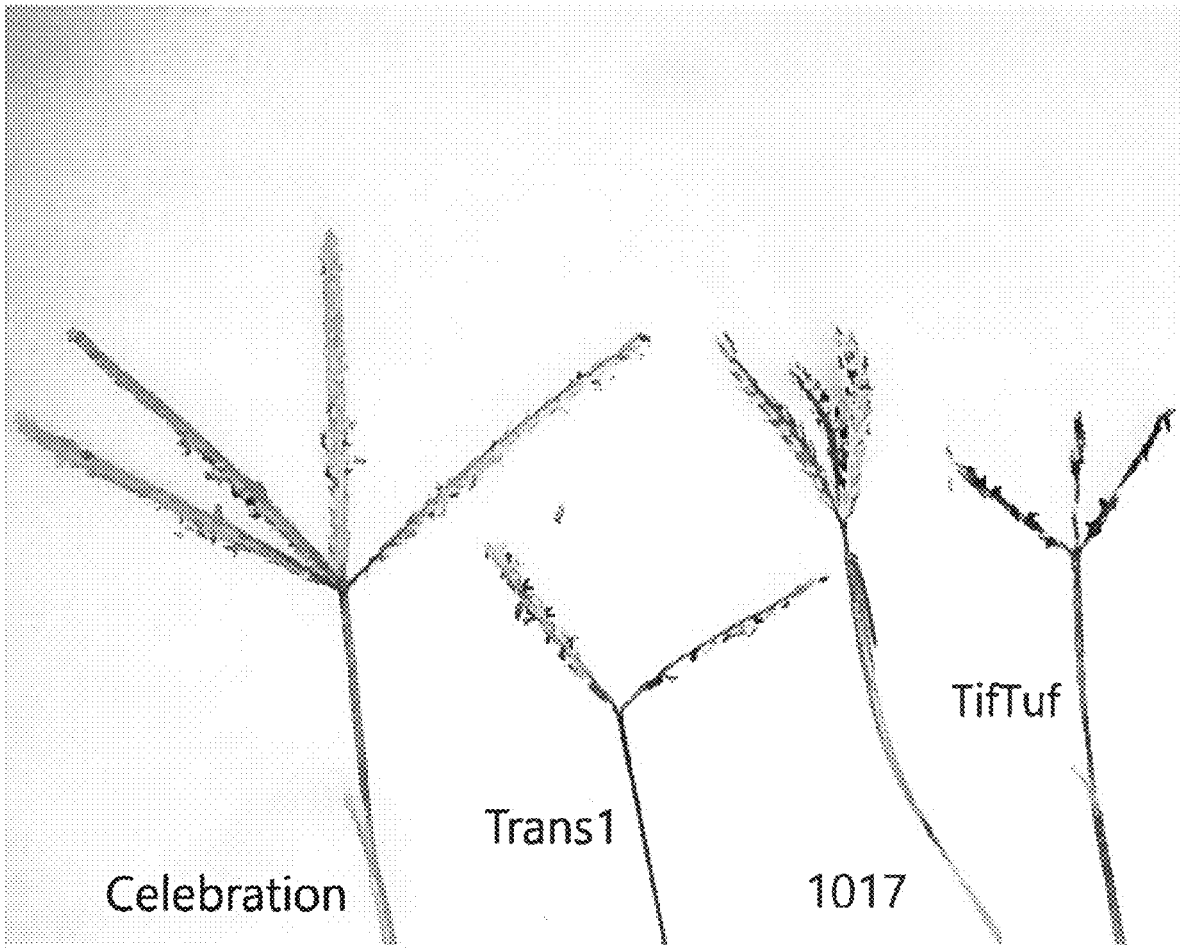

FIG. 2. Photo comparing the seed head of 'MSB-1017' (shown as 1017) with the female parent 'Riley's Super Sport', shown as Celebration, the male parent 'Trans1' and the commercial line 'TifTuf'. The photo was taken on Jun. 6, 2023. Plugs were taken from field plots and planted in pots in the greenhouse in Starkville, Mississippi.

Figure 3:
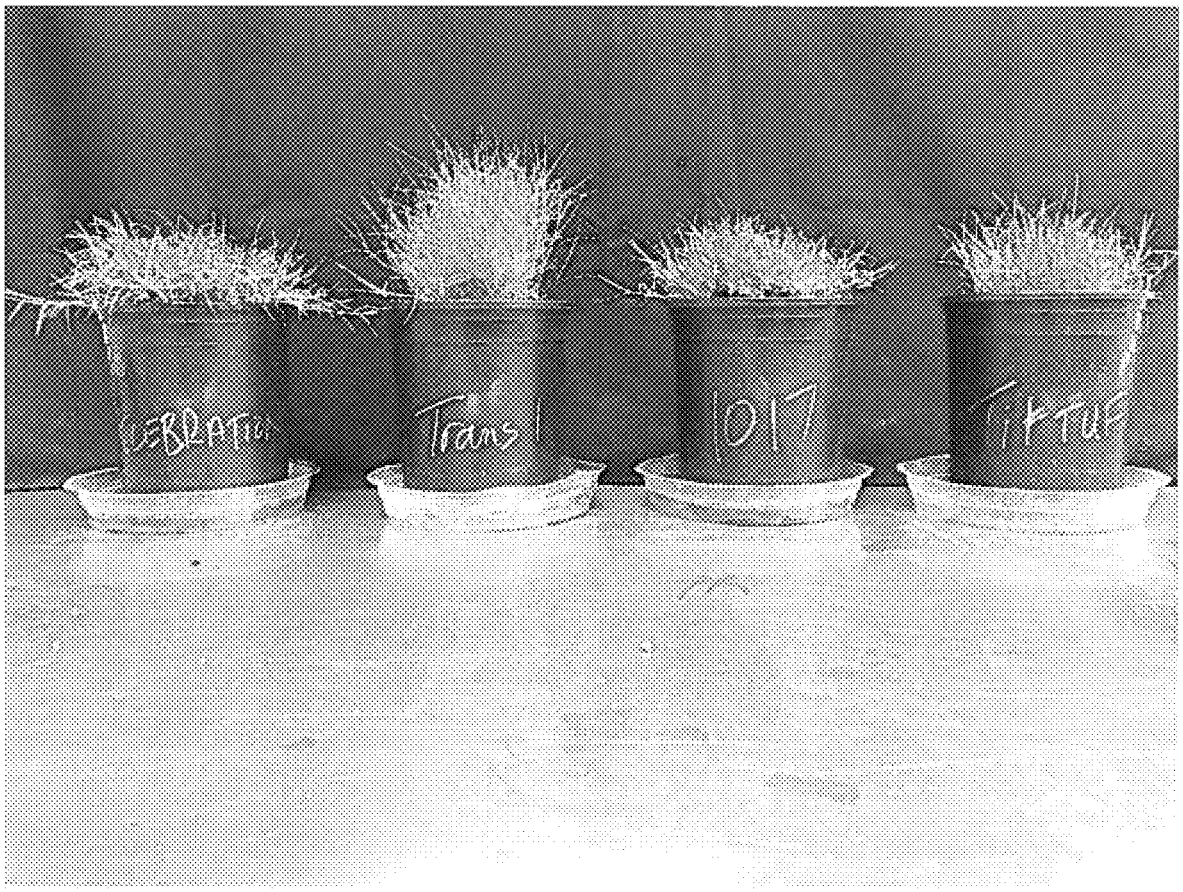

FIG. 3. Photo taken on Jun. 16, 2023 in Starkville, Mississippi comparing the grass of 'MSB-1017' (shown as 1017) with the female parent 'Riley's Super Sport', shown as Celebration, the male parent 'Trans1' and the commercial line 'TifTuf'.

Figure 4:
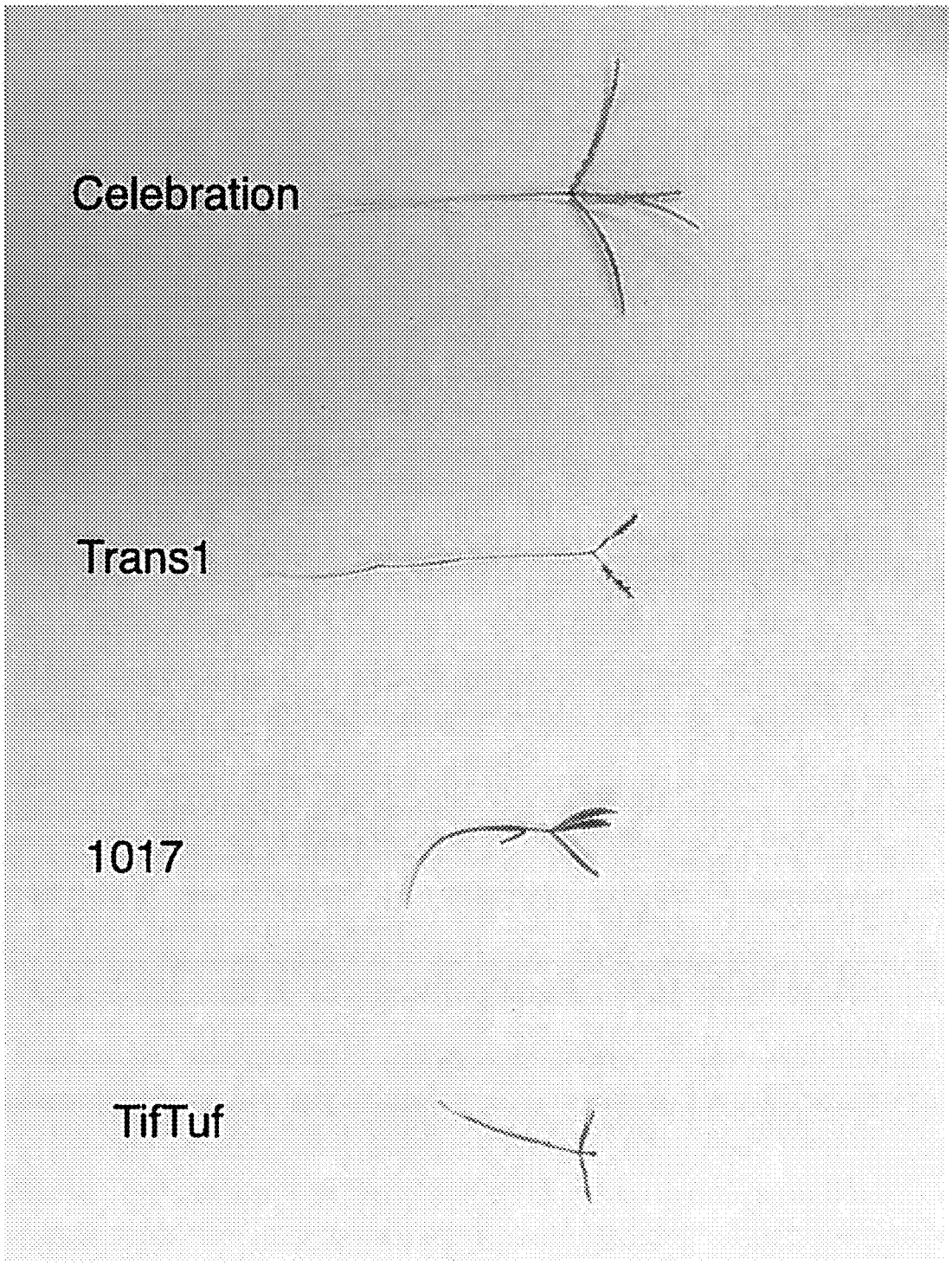

FIG. 4. Photo taken on Jun. 20, 2023 in Starkville, Mississippi comparing the spike and seed head of 'MSB-1017' (shown as 1017) with the female parent 'Riley's Super Sport', shown as Celebration, the male parent 'Trans1' and the commercial line 'TifTuf'.

Figure 5:
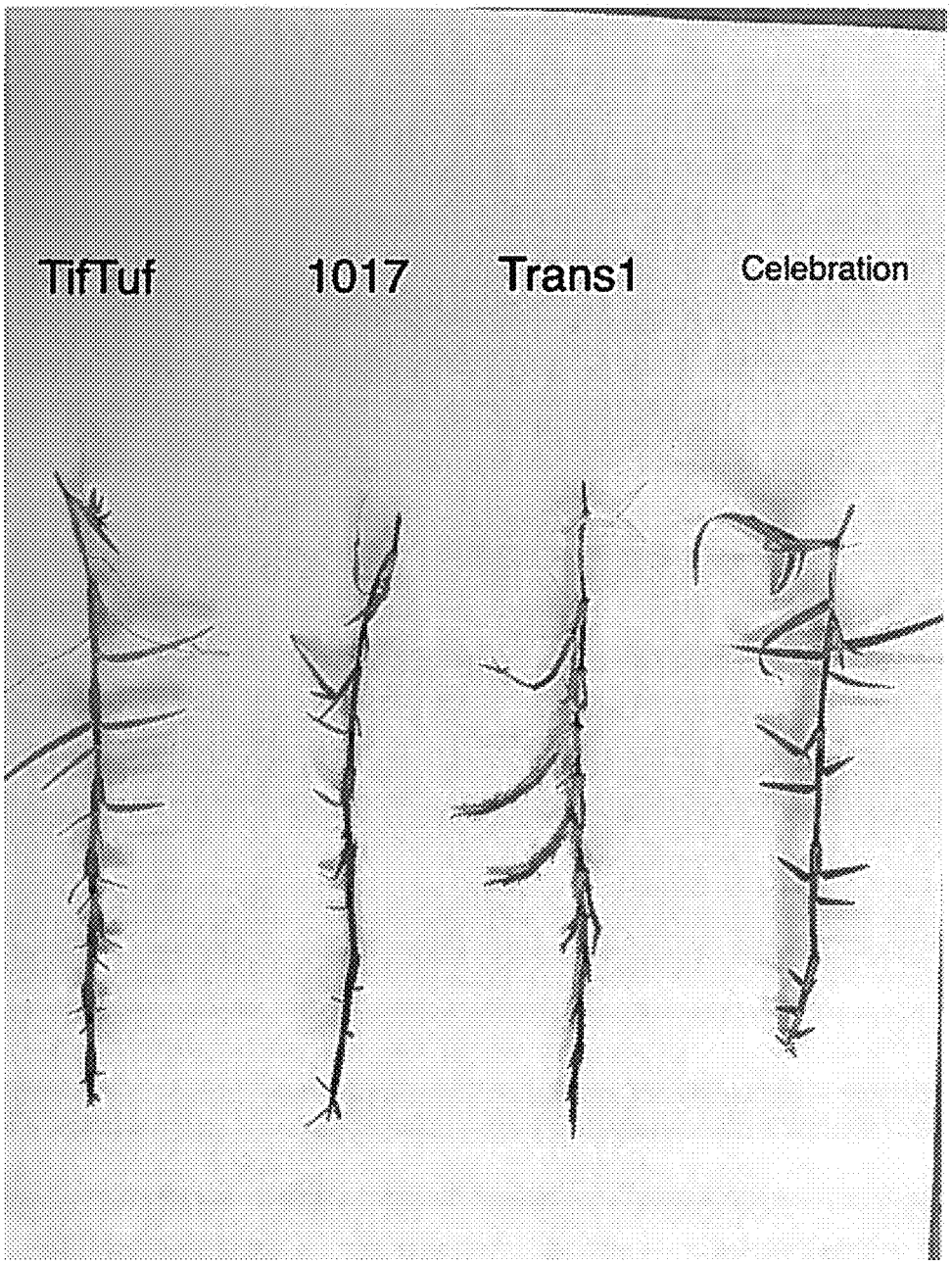

FIG. 5. Photo taken on Jun. 29, 2023 in Starkville, Mississippi comparing the rhizomes of 'MSB-1017' (shown as 1017) with the female parent 'Riley's Super Sport', shown as Celebration, the male parent 'Trans1' and the commercial line 'TifTuf'.

Figure 6:
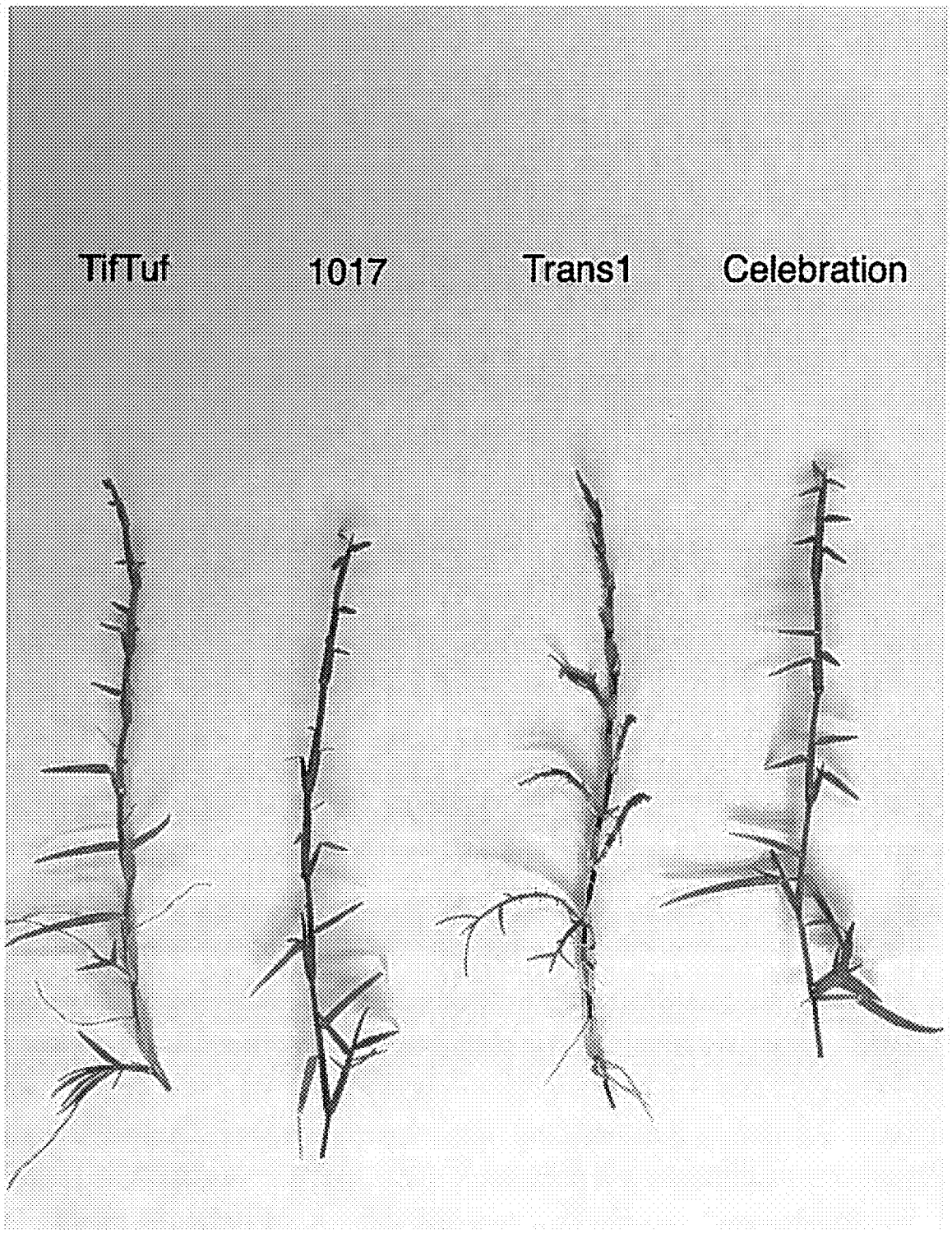

FIG. 6. Photo taken on Jul. 18, 2023 in Starkville, Mississippi comparing the rhizomes of 'MSB-1017' (shown as 1017) with the female parent 'Riley's Super Sport', shown as Celebration, the male parent 'Trans1' and the commercial line 'TifTuf'.

Figure 7:
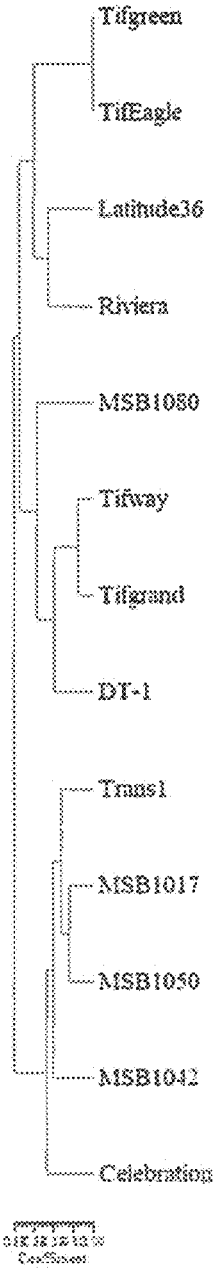

FIG. 7 is a pictorial representation of a phylogenetic tree that shows 'MSB-1017' is genetically different from the other bermudagrass cultivars analyzed.

DESCRIPTION OF THE NEW VARIETY

The following detailed descriptions set forth the distinctive characteristics of 'MSB-1017'.

'MSB-1017' has been tested in the 2019 National Turfgrass Evaluation Program (NTEP trial) bermudagrass test which involves 19 environments at 16 locations where each location is identified by a code in column 3 (Table 1).

TABLE 1

| State | Location | Code |
|---|---|---|
| Alabama | Auburn | AL1 |
| Arkansas | Fayetteville | AR1 |
| California | Riverside (Drought) | CA3 |
| Florida | Fort Lauderdale | FL5 |
| Florida | Jay | FL3 |
| Indiana | West Lafayette | IN1 |
| Kansas | Wichita | KS2 |
| Kentucky | Lexington | KY1 |
| Mississippi | Mississippi State | MS1 |
| Missouri | Columbia | MO1 |
| New Mexico | Las Cruces | NM1 |
| New Mexico | Las Cruces (Salinity) | NM2 |
| North Carolina | Raleigh (Traffic) | NC1 |
| Oklahoma | Stillwater | OK1 |
| Oklahoma | Stillwater (Divot Recovery) | OK2 |
| Tennessee | Knoxville | TN1 |
| Texas | College Station (Drought) | TX2 |
| Texas | College Station (Shade) | TX3 |
| Virginia | Blacksburg | VA1 |

Classification:

*Family*.—Poaceae.

*Species*.—*Cynodon dactylon* x *Cynodon transvaalensis*.

*Common name*.—Bermudagrass.

*Variety*.—'MSB-1017'.

Parentage:

*Female*.—'Riley's Super Sport' (U.S. Plant Pat. No. 11,181).

*Male*.—'trans1' (unpatented).

A total of 22 vegetative bermudagrass entries (17 experimental lines and 5 commercial standards) were tested in the following trials:

1) 2019 NTEP bermudagrass test shown in Table 1;
2) an evaluation trial at Mississippi State University research facility in 2016 (MSU 2016 trial), and a total of 33 entries (31 experimental lines and 2 commercial standards) were included;
3) a home lawn trial established in 2017 at Mississippi State University research facility (MSU 2017 trial), with a total of 15 entries (13 experimental lines and 2 commercial standards) included; and
4) a fourth trial at Mississippi State University research facility in 2018 (MSU 2018 trial), with a total of 26 entries (23 experimental lines and 3 commercial standards) included.

The following are detailed botanical descriptions of the characteristics of this new cultivar, based upon the first year (2020) data of the 2019 NTEP trial, three years (2016-2018) data of MSU 2016 trial, one year (2017-2018) data of the MSU 2017 trial, and two years (2020-2021) data of MSU 2018 trial.

Turfgrass quality ratings are based on a combination of color, density, uniformity, texture, and disease or environmental stress. Quality ratings are based on 1-9 scale, with 9 being the best and 1 being poorest.

Data from the NTEP trial revealed that 'MSB-1017', along with commercial standards 'Tahoma 31' and 'Tiftuf', exhibited highest quality (mean quality rating of 6.4) when averaged across all 13 testing locations (Table 2).

Patent status of varieties listed in Tables 2-17: 'OKC1876', U.S. Plant Pat. No. 35,548; 'TifEagle', U.S. Plant Pat. No. 11,163; 'TifGrand', U.S. Plant Pat. No. 21,017; MSB-04-264', U.S. Plant Pat. No. 23,407; 'Riviera', U.S. PVP Certificate No. 009500227; 'Astro', unpatented; 'Latitude 36', U.S. Plant Pat. No. 24,271; 'Tahoma 31', patented under the name 'OKC 1131' U.S. Plant Pat. No. 31,695; 'OKC 1876', U.S. Plant Pat. No. 35,548, 'TifTuf', experimental name 'DT-1', U.S. Plant Pat. No. 27,392; FB 1628, unpatented; OKC1873, unpatented; MSB-1042, unpatented; MSB-1050, unpatented; MSB-1026, unpatented; FB 1630, unpatented; *Tifway, unpatented; MSB-1048, unpatented; JSC 80V, unpatented; JSC 77V, unpatented; OKC1406, unpatented; OKC1682, unpatented; OKC1666, unpatented; FB 1903, unpatented; FB 1902, unpatented; MSB-1075, unpatented.

TABLE 2

Turfgrass quality of 22 vegetative bermudagrass entries evaluated in the 2019 NTEP trial. (9 = very high; 1 = low).

| Entry | VA1 | IN1 | AR1 | KS2 | MO1 | OK1 | NM1 |
|---|---|---|---|---|---|---|---|
| MSB-1017 | 7.3 | 6.5 | 7.4 | 5.2 | 6.8 | 6.2 | 6.3 |
| *Tahoma 31 | 6.6 | 6.6 | 7.4 | 5.1 | 7.5 | 6.4 | 6.5 |
| *Tiftuf | 7.5 | 6.9 | 7.5 | 5.9 | 7.0 | 6.3 | 4.9 |
| FB 1628 | 6.9 | 6.9 | 7.4 | 5.4 | 6.4 | 6.4 | 5.1 |
| OKC1876 | 7.0 | 6.7 | 7.5 | 5.3 | 6.2 | 6.3 | 5.8 |
| *Latitude 36 | 7.2 | 6.6 | 6.9 | 5.7 | 7.0 | 6.1 | 5.9 |
| OKC1873 | 6.9 | 6.3 | 7.4 | 5.3 | 5.3 | 6.1 | 6.3 |
| MSB-1042 | 7.3 | 6.6 | 7.1 | 6.0 | 6.9 | 6.0 | 5.0 |
| MSB-1050 | 5.9 | 6.3 | 7.5 | 4.2 | 6.6 | 6.2 | 5.9 |
| *Astro | 7.1 | 6.1 | 6.6 | 5.4 | 5.6 | 5.8 | 6.7 |
| MSB-1026 | 6.2 | 6.5 | 7.3 | 4.8 | 4.8 | 6.2 | 4.7 |
| FB 1630 | 6.5 | 6.1 | 6.6 | 4.9 | 4.9 | 5.9 | 6.3 |
| *Tifway | 6.3 | 6.3 | 7.1 | 5.0 | 5.5 | 6.0 | 5.5 |
| MSB-1048 | 6.7 | 6.2 | 6.6 | 5.2 | 5.8 | 5.8 | 5.4 |
| JSC 80V | 6.5 | 5.9 | 6.2 | 5.5 | 4.9 | 5.7 | 6.4 |
| JSC 77V | 5.7 | 6.3 | 6.4 | 5.1 | 5.3 | 5.9 | 4.7 |
| OKC1406 | 6.6 | 6.2 | 6.4 | 5.4 | 5.7 | 5.6 | 4.8 |
| OKC1682 | 5.7 | 5.9 | 6.4 | 5.2 | 5.8 | 5.8 | 5.7 |
| OKC1666 | 7.3 | 5.8 | 6.1 | 5.9 | 4.8 | 5.2 | 5.3 |
| FB 1903 | 5.4 | 5.4 | 6.6 | 4.3 | 3.6 | 5.6 | 6.7 |
| FB 1902 | 5.3 | 5.5 | 6.2 | 4.8 | 4.5 | 5.5 | 6.0 |
| MSB-1075 | 4.1 | 5.2 | 5.9 | 3.2 | 3.2 | 5.4 | 5.9 |
| LSD (0.05) | 0.8 | 0.8 | 0.8 | 0.8 | 0.8 | 0.8 | 0.8 |
| C.V. (%) | 7.9 | 8.3 | 7.5 | 10.0 | 9.1 | 8.7 | 9.0 |

| Entry | FL5 | TN1 | KY1 | FL3 | AL1 | MS1 | Mean |
|---|---|---|---|---|---|---|---|
| MSB-1017 | 7.4 | 5.4 | 6.3 | 7.3 | 5.9 | 5.6 | 6.4 |
| *Tahoma 31 | 7.7 | 5.8 | 6.5 | 6.8 | 5.3 | 5.6 | 6.4 |
| *Tiftuf | 7.1 | 6.1 | 6.5 | 6.5 | 5.9 | 5.4 | 6.4 |
| FB 1628 | 8.1 | 6.1 | 6.7 | 6.8 | 5.7 | 5.5 | 6.4 |
| OKC1876 | 7.4 | 5.9 | 6.5 | 7.1 | 5.8 | 5.7 | 6.4 |
| *Latitude 36 | 7.3 | 5.8 | 6.3 | 6.4 | 5.2 | 5.2 | 6.3 |
| OKC1873 | 6.2 | 6.0 | 6.3 | 7.0 | 5.6 | 5.8 | 6.2 |
| MSB-1042 | 6.4 | 6.0 | 6.2 | 6.0 | 5.3 | 5.1 | 6.1 |

TABLE 2-continued

Turfgrass quality of 22 vegetative bermudagrass entries evaluated in the 2019 NTEP trial. (9 = very high; 1 = low).

| | | | | | | | |
|---|---|---|---|---|---|---|---|
| MSB-1050 | 7.6 | 5.4 | 6.2 | 7.0 | 5.3 | 5.6 | 6.1 |
| *Astro | 7.1 | 5.5 | 6.1 | 6.8 | 5.2 | 5.4 | 6.1 |
| MSB-1026 | 7.4 | 6.2 | 6.6 | 6.8 | 5.6 | 5.7 | 6.1 |
| FB 1630 | 7.7 | 5.6 | 6.3 | 6.9 | 5.0 | 5.4 | 6.0 |
| *Tifway | 6.7 | 6.0 | 6.2 | 6.4 | 5.1 | 5.4 | 6.0 |
| MSB-1048 | 7.2 | 5.5 | 6.1 | 6.3 | 5.0 | 5.0 | 5.9 |
| JSC 80V | 6.5 | 6.0 | 6.0 | 6.1 | 4.4 | 5.1 | 5.8 |
| JSC 77V | 7.7 | 6.3 | 6.4 | 5.7 | 4.4 | 5.0 | 5.8 |
| OKC1406 | 7.0 | 5.7 | 6.0 | 5.8 | 4.7 | 4.7 | 5.7 |
| OKC1682 | 6.2 | 6.1 | 6.0 | 5.4 | 3.9 | 4.9 | 5.6 |
| OKC1666 | 5.1 | 5.7 | 5.6 | 5.6 | 4.7 | 4.7 | 5.5 |
| FB 1903 | 5.8 | 5.8 | 5.9 | 6.6 | 4.4 | 5.7 | 5.5 |
| FB 1902 | 5.5 | 6.1 | 5.8 | 5.4 | 3.7 | 5.0 | 5.3 |
| MSB-1075 | 7.5 | 5.4 | 5.9 | 6.3 | 3.7 | 5.2 | 5.1 |
| LSD (0.05) | 0.8 | 0.8 | 0.8 | 0.8 | 0.8 | 0.8 | 0.6 |
| C.V. (%) | 7.5 | 8.8 | 8.3 | 8.0 | 10.3 | 9.7 | 6.3 |

*Standard entries

In MSU 2016 trial, 'MSB-1017' ranked 1st in mean quality ratings (7.0) and was ranked significantly higher than its female parent 'Riley's Super Sport' (Table 3).

TABLE 3

Turf quality of experimental bermudagrass entries planted at Mississippi State University in 2016 and evaluated over three years. (9 = very high; 1 = low).

| Entry | 2016 | 2017 | 2018 | Mean |
|---|---|---|---|---|
| MSB-1017 | 7.7 | 6.8 | 6.6 | 7.0 |
| MSB-1026 | 7.3 | 6.4 | 7.0 | 6.9 |
| *Tifway | 7.7 | 6.5 | 6.3 | 6.8 |
| MSB-1004 | 6.9 | 6.7 | 6.7 | 6.8 |
| MSB-1010 | 7.4 | 6.5 | 6.2 | 6.7 |
| MSB-1006 | 6.7 | 6.3 | 6.7 | 6.6 |
| MSB-1012 | 6.7 | 6.5 | 6.4 | 6.5 |
| MSB-1013 | 6.8 | 6.5 | 6.3 | 6.5 |
| MSB-1022 | 6.4 | 6.5 | 6.5 | 6.5 |
| MSB-1005 | 6.4 | 6.2 | 6.1 | 6.2 |
| MSB-1016 | 6.4 | 6.2 | 5.8 | 6.1 |
| MSB-1008 | 6.0 | 6.2 | 6.1 | 6.1 |
| *'Riley's Super Sport' | 6.1 | 6.3 | 5.9 | 6.1 |
| MSB-1002 | 5.9 | 6.3 | 6.0 | 6.1 |
| MSB-1011 | 6.2 | 6.3 | 5.7 | 6.1 |
| MSB-1014 | 5.9 | 6.2 | 6.0 | 6.0 |
| MSB-1018 | 6.6 | 5.9 | 5.5 | 6.0 |
| MSB-1009 | 6.1 | 6.0 | 5.8 | 6.0 |
| MSB-1019 | 6.0 | 6.2 | 5.8 | 6.0 |
| MSB-1001 | 6.3 | 6.0 | 5.7 | 6.0 |
| MSB-1021 | 6.1 | 5.9 | 5.5 | 5.9 |
| MSB-1015 | 6.1 | 5.8 | 5.5 | 5.8 |
| MSB-1003 | 6.6 | 5.8 | 4.8 | 5.7 |
| MSB-1020 | 5.8 | 5.4 | 4.8 | 5.3 |
| MSB-1025 | 5.9 | 5.3 | 4.8 | 5.3 |
| MSB-1027 | 5.1 | 5.5 | 5.0 | 5.2 |
| MSB-1007 | 5.4 | 5.2 | 4.9 | 5.2 |
| MSB-1029 | 5.6 | 5.0 | 4.8 | 5.1 |
| MSB-1028 | 5.3 | 4.9 | 4.6 | 5.0 |
| MSB-1024 | 5.3 | 5.2 | 4.1 | 4.9 |
| MSB-1031 | 3.0 | 5.1 | 5.5 | 4.4 |
| MSB-1033 | 2.9 | 4.0 | 5.1 | 4.0 |
| MSB-1002 | 2.6 | 4.6 | 4.7 | 3.7 |
| LSD (0.05) | 0.8 | 0.4 | 0.6 | 0.4 |
| C.V. (%) | 8.7 | 4.5 | 6.6 | 6.9 |

*Standard entries

Similarly, in MSU 2018 trial, 'MSB-1017' ranked 4th in mean quality ratings (6.6) and was ranked significantly higher than 'Riley's Super Sport' (Table 4).

TABLE 4

Turf quality, seedhead, and leaf texture of experimental bermudagrass entries planted at Mississippi State University in 2018 and evaluated over two years. (9 = very high; 1 = low).

| | Quality | | | Seedhead | | |
|---|---|---|---|---|---|---|
| Entry | 2020 | 2021 | Mean | 2020 | 2021 | Mean |
| MSB-1050 | 7.2 | 6.5 | 6.9 | 8.7 | 8.9 | 8.8 |
| MSB-1080 | 6.8 | 6.8 | 6.8 | 8.5 | 7.8 | 8.2 |
| MSB-1048 | 6.8 | 6.5 | 6.7 | 8.0 | 8.3 | 8.1 |
| MSB-1017 | 6.8 | 6.4 | 6.6 | 8.2 | 8.1 | 8.2 |
| MSB-1046 | 6.8 | 6.3 | 6.6 | 8.5 | 7.9 | 8.2 |
| MSB-1075 | 6.5 | 6.3 | 6.4 | 9.0 | 8.4 | 8.7 |
| *Tiftuf | 6.5 | 6.5 | 6.5 | 7.6 | 7.4 | 7.5 |
| *Tifway | 6.5 | 6.4 | 6.5 | 8.5 | 7.9 | 8.2 |
| MSB-1044 | 6.4 | 6.1 | 6.3 | 8.1 | 7.8 | 7.9 |
| MSB-1047 | 6.4 | 6.1 | 6.3 | 7.7 | 7.4 | 7.5 |
| MSB-1042 | 6.3 | 6.2 | 6.3 | 8.1 | 8.0 | 8.1 |
| MSB-1026 | 6.3 | 6.1 | 6.2 | 9.0 | 9.0 | 9.0 |
| MSB-1041 | 5.9 | 5.5 | 5.7 | 8.7 | 8.4 | 8.6 |
| MSB-1067 | 5.8 | 5.7 | 5.7 | 8.3 | 8.3 | 8.3 |
| *'Riley's Super Sport' | 5.7 | 5.7 | 5.7 | 5.7 | 5.9 | 5.8 |
| MSB-1012 | 5.7 | 5.6 | 5.7 | 6.7 | 7.0 | 6.8 |
| MSB-1079 | 5.7 | 5.3 | 5.5 | 5.4 | 5.5 | 5.4 |
| MSB-1069 | 5.6 | 5.6 | 5.6 | 8.1 | 7.8 | 8.0 |
| MSB-1059 | 5.3 | 5.4 | 5.4 | 7.5 | 6.9 | 7.2 |
| MSB-1073 | 5.2 | 5.2 | 5.2 | 5.9 | 6.1 | 6.0 |
| MSB-1077 | 5.1 | 4.8 | 5.0 | 5.3 | 5.3 | 5.3 |
| MSB-1072 | 5.0 | 4.4 | 4.7 | 5.7 | 5.5 | 5.6 |
| MSB-1074 | 4.7 | 4.3 | 4.5 | 4.9 | 4.9 | 4.9 |
| MSB-1076 | 4.4 | 4.3 | 4.4 | 4.3 | 4.5 | 4.4 |
| MSB-1078 | 4.2 | 3.3 | 3.8 | 4.7 | 5.5 | 5.1 |
| MSB-1081 | 3.9 | 3.3 | 3.6 | 5.2 | 4.9 | 5.1 |
| LSD (0.05) | 0.6 | 0.4 | 0.4 | 0.7 | 0.5 | 0.5 |
| C.V. (%) | 15.3 | 17.4 | 16.2 | 21.7 | 19.6 | 20.5 |

| | Leaf texture | | |
|---|---|---|---|
| Entry | 2020 | 2021 | Mean |
| MSB-1050 | 8.0 | 8.0 | 8.0 |
| MSB-1080 | 6.8 | 7.0 | 6.9 |
| MSB-1048 | 7.0 | 7.0 | 7.0 |
| MSB-1017 | 7.0 | 7.0 | 7.0 |
| MSB-1046 | 6.7 | 6.3 | 6.5 |
| MSB-1075 | 6.7 | 6.7 | 6.7 |
| *Tiftuf | 6.2 | 6.7 | 6.4 |
| *Tifway | 6.2 | 6.3 | 6.3 |
| MSB-1044 | 6.3 | 6.0 | 6.2 |
| MSB-1047 | 6.0 | 6.0 | 6.0 |
| MSB-1042 | 6.7 | 6.3 | 6.5 |
| MSB-1026 | 6.3 | 6.0 | 6.2 |
| MSB-1041 | 5.8 | 5.3 | 5.6 |
| MSB-1067 | 6.2 | 6.0 | 6.1 |
| *'Riley's Super Sport' | 5.0 | 5.7 | 5.3 |
| MSB-1012 | 5.5 | 5.0 | 5.3 |
| MSB-1079 | 6.2 | 6.3 | 6.3 |
| MSB-1069 | 6.3 | 6.0 | 6.2 |
| MSB-1059 | 6.0 | 6.3 | 6.2 |
| MSB-1073 | 5.0 | 5.7 | 5.3 |
| MSB-1077 | 5.7 | 5.3 | 5.5 |
| MSB-1072 | 5.2 | 5.3 | 5.3 |
| MSB-1074 | 5.2 | 4.7 | 4.9 |
| MSB-1076 | 5.8 | 6.3 | 6.1 |
| MSB-1078 | 5.5 | 5.3 | 5.4 |
| MSB-1081 | 4.7 | 4.7 | 4.7 |
| LSD (0.05) | 0.5 | 0.7 | 0.4 |
| C.V. (%) | 12.4 | 12.8 | 12.3 |

*Standard entries

Leaf texture is a measure or estimate of leaf width. The visual rating of texture is based on 1-9 scale with 1 equaling coarse and 9 equal fine. NTEP trial revealed that 'MSB-1017' ranked 3rd across nine locations, with a mean rating of 7.5 (Table 5), which was slightly lower than two MSU experimental lines, MSB-1050 and MSB-1048, both had a mean rating of 7.6 (Table 5).

TABLE 5

Leaf texture ratings of 22 vegetative bermudagrass entries evaluated in the 2019 NTEP trial. (9 = very fine; 1 = coarse).

| Entry | AL1 | AR1 | FL3 | IN1 | KS2 |
|---|---|---|---|---|---|
| MSB-1050 | 9.0 | 7.3 | 8.0 | 7.7 | 6.3 |
| MSB-1048 | 7.7 | 7.7 | 7.7 | 7.0 | 8.7 |
| MSB-1017 | 7.3 | 7.7 | 7.3 | 7.0 | 8.0 |
| OKC1666 | 7.3 | 7.3 | 8.7 | 7.7 | 8.7 |
| OKC1876 | 6.7 | 8.0 | 7.7 | 7.3 | 7.3 |
| MSB-1042 | 7.3 | 8.0 | 7.3 | 8.0 | 7.7 |
| *Tiftuf | 7.7 | 9.0 | 6.3 | 6.3 | 7.0 |
| MSB-1026 | 7.0 | 7.7 | 7.0 | 7.0 | 7.3 |
| OKC1873 | 7.3 | 8.0 | 7.3 | 7.0 | 7.0 |
| *Tifway | 6.3 | 8.3 | 7.0 | 7.0 | 6.7 |
| *Latitude 36 | 6.3 | 7.7 | 7.3 | 7.3 | 7.7 |
| OKC1406 | 6.3 | 8.0 | 7.3 | 7.0 | 6.3 |
| FB 1628 | 7.0 | 7.0 | 5.3 | 7.3 | 5.7 |
| OKC1682 | 5.0 | 7.0 | 6.3 | 6.7 | 7.7 |
| *Tahoma 31 | 5.3 | 8.3 | 6.3 | 7.0 | 5.7 |
| MSB-1075 | 5.0 | 5.3 | 8.3 | 5.7 | 7.3 |
| JSC 80V | 4.3 | 7.3 | 6.7 | 7.0 | 7.0 |
| JSC 77V | 5.3 | 7.3 | 7.0 | 6.0 | 7.0 |
| *Astro | 5.3 | 6.7 | 4.7 | 6.3 | 5.7 |
| FB 1903 | 6.7 | 7.0 | 4.0 | 5.3 | 4.7 |
| FB 1902 | 4.3 | 6.7 | 4.0 | 7.0 | 5.3 |
| FB 1630 | 5.3 | 6.0 | 5.0 | 5.7 | 4.7 |
| LSD (0.05) | 1.8 | 1.0 | 1.0 | 0.8 | 1.3 |
| C.V. (%) | 17.3 | 8.3 | 9.6 | 7.4 | 11.6 |

| Entry | MS1 | NM1 | OK1 | TN1 | Mean |
|---|---|---|---|---|---|
| MSB-1050 | 7.0 | 6.3 | 8.0 | 9.0 | 7.6 |
| MSB-1048 | 6.0 | 7.0 | 7.3 | 9.0 | 7.6 |
| MSB-1017 | 7.0 | 6.7 | 7.7 | 9.0 | 7.5 |
| OKC1666 | 6.3 | 5.7 | 6.3 | 8.7 | 7.4 |
| OKC1876 | 7.0 | 6.3 | 7.3 | 9.0 | 7.4 |
| MSB-1042 | 6.3 | 4.7 | 7.0 | 9.0 | 7.3 |
| *Tiftuf | 6.3 | 6.3 | 6.7 | 9.0 | 7.2 |
| MSB-1026 | 6.0 | 7.0 | 7.0 | 8.3 | 7.1 |
| OKC1873 | 5.7 | 6.0 | 7.0 | 9.0 | 7.1 |
| *Tifway | 6.0 | 6.7 | 7.0 | 9.0 | 7.1 |
| *Latitude 36 | 5.7 | 5.7 | 7.0 | 8.7 | 7.0 |
| OKC1406 | 5.7 | 6.0 | 7.0 | 9.0 | 7.0 |
| FB 1628 | 6.0 | 6.7 | 7.0 | 8.7 | 6.7 |
| OKC1682 | 6.3 | 6.0 | 6.7 | 8.7 | 6.7 |
| *Tahoma 31 | 6.0 | 6.0 | 6.7 | 9.0 | 6.7 |
| MSB-1075 | 6.3 | 6.3 | 7.0 | 8.7 | 6.7 |
| JSC 80V | 6.0 | 5.7 | 7.0 | 9.0 | 6.7 |
| JSC 77V | 6.0 | 5.7 | 6.3 | 9.0 | 6.6 |
| *Astro | 5.7 | 7.3 | 6.3 | 8.3 | 6.3 |
| FB 1903 | 6.0 | 6.7 | 6.7 | 8.0 | 6.1 |
| FB 1902 | 5.7 | 7.0 | 6.0 | 8.0 | 6.0 |
| FB 1630 | 6.0 | 6.0 | 6.0 | 8.3 | 5.9 |
| LSD (0.05) | 0.6 | 1.2 | 0.6 | 0.6 | 1.0 |
| C.V. (%) | 6.3 | 11.6 | 5.7 | 4.0 | 9.5 |

MSU 2016 trial revealed that 'MSB-1017' had the highest leaf texture rating (7.1) and was ranked significantly higher than 'Riley's Super Sport' (Table 6).

TABLE 6

Leaf texture rating of experimental bermudagrass genotypes planted at Mississippi State University in 2016 and evaluated over three growing seasons. (9 = very fine; 1 = low).

| Entry | 2016 | 2017 | 2018 | Mean |
|---|---|---|---|---|
| MSB-1017 | 7.0 | 6.7 | 7.7 | 7.1 |
| MSB-1013 | 6.7 | 7.0 | 7.7 | 7.1 |
| MSB-1010 | 7.0 | 6.3 | 7.7 | 7.0 |

TABLE 6-continued

Leaf texture rating of experimental bermudagrass genotypes planted at Mississippi State University in 2016 and evaluated over three growing seasons. (9 = very fine; 1 = low).

| Entry | 2016 | 2017 | 2018 | Mean |
|---|---|---|---|---|
| MSB-1016 | 7.0 | 6.0 | 7.3 | 6.8 |
| MSB-1026 | 6.0 | 6.7 | 7.7 | 6.8 |
| MSB-1018 | 7.0 | 6.0 | 7.3 | 6.8 |
| MSB-1032 | 6.7 | 6.0 | 7.3 | 6.8 |
| *Tifway | 7.0 | 6.0 | 7.0 | 6.7 |
| MSB-1022 | 6.3 | 6.0 | 7.7 | 6.7 |
| MSB-1033 | 6.3 | 5.7 | 7.0 | 6.3 |
| MSB-1004 | 6.0 | 6.0 | 7.0 | 6.3 |
| MSB-1002 | 6.0 | 6.0 | 7.0 | 6.3 |
| MSB-1009 | 6.7 | 5.3 | 6.3 | 6.1 |
| MSB-1031 | 5.0 | 6.0 | 7.0 | 6.0 |
| MSB-1014 | 5.7 | 5.7 | 6.7 | 6.0 |
| MSB-1012 | 6.0 | 5.3 | 6.3 | 5.9 |
| MSB-1006 | 6.0 | 5.3 | 6.3 | 5.9 |
| MSB-1005 | 6.0 | 5.3 | 6.0 | 5.8 |
| MSB-1015 | 5.0 | 5.7 | 6.3 | 5.7 |
| MSB-1027 | 5.7 | 5.3 | 6.0 | 5.7 |
| MSB-1008 | 5.3 | 5.0 | 6.3 | 5.6 |
| MSB-1020 | 5.7 | 5.0 | 6.0 | 5.6 |
| MSB-1028 | 5.0 | 5.3 | 6.0 | 5.4 |
| MSB-1021 | 5.3 | 5.0 | 6.0 | 5.4 |
| MSB-1003 | 5.3 | 4.7 | 6.0 | 5.3 |
| MSB-1024 | 5.3 | 5.0 | 5.7 | 5.3 |
| MSB-1001 | 5.3 | 4.7 | 6.0 | 5.3 |
| *'Riley's Super Sport' | 5.0 | 5.0 | 5.7 | 5.2 |
| MSB-1019 | 5.0 | 4.7 | 5.3 | 5.0 |
| MSB-1029 | 5.3 | 4.3 | 5.3 | 5.0 |
| MSB-1025 | 6.0 | 4.0 | 5.0 | 5.0 |
| MSB-1007 | 5.0 | 4.3 | 5.3 | 4.9 |
| MSB-1011 | 5.0 | 4.0 | 5.3 | 4.8 |
| LSD (0.05) | 0.6 | 0.8 | 0.7 | 0.4 |
| C.V. (%) | 6.3 | 8.8 | 7.1 | 7.5 |

*Standard entries

Genetic color reflects the inherent color of the grasses. It is based on a visual rating scale of 1-9 with 9 being dark green and 1 being light green. In the 2019 NTEP trial, genetic color ratings were taken at ten locations when the tested bermudagrasses were actively growing and were not stressed (Table 7). 'MSB-1017' showed good genetic color ratings, ranking 5h (tied with another entry FB 1903) with a mean rating of 6.6, which was not statistically different from the best rating (Table 7).

TABLE 7

Genetic color of 22 vegetative bermudagrass entries evaluated in the NTEP trial. (9 = dark green; 1 = light green).

| Entry | AL1 | AR1 | FL3 | IN1 | KS2 | MO1 |
|---|---|---|---|---|---|---|
| MSB-1026 | 8.0 | 7.0 | 8.7 | 8.7 | 7.7 | 3.7 |
| FB 1628 | 6.7 | 7.3 | 7.7 | 8.7 | 8.0 | 5.3 |
| FB 1902 | 8.3 | 6.3 | 7.0 | 8.0 | 8.7 | 5.7 |
| *Tifway | 6.7 | 7.0 | 7.3 | 7.0 | 6.3 | 6.3 |
| FB 1903 | 5.3 | 5.7 | 8.0 | 8.3 | 8.7 | 4.0 |
| MSB-1017 | 7.7 | 7.7 | 7.3 | 7.7 | 7.3 | 4.7 |
| MSB-1050 | 5.0 | 6.0 | 8.7 | 8.0 | 7.0 | 5.0 |
| OKC1876 | 7.0 | 7.7 | 6.3 | 8.0 | 6.7 | 5.7 |
| MSB-1075 | 6.0 | 6.3 | 8.0 | 7.7 | 9.0 | 2.3 |
| OKC1682 | 4.7 | 7.0 | 7.0 | 6.3 | 7.3 | 6.3 |
| FB 1630 | 5.7 | 5.7 | 7.7 | 7.7 | 7.7 | 4.7 |
| *Tahoma 31 | 3.7 | 6.3 | 7.0 | 8.3 | 7.7 | 6.3 |
| MSB-1048 | 6.0 | 7.3 | 6.7 | 7.0 | 7.7 | 5.3 |
| *Latitude 36 | 6.3 | 7.3 | 6.7 | 7.3 | 5.0 | 6.3 |
| *Tiftuf | 5.0 | 7.7 | 6.3 | 7.0 | 5.3 | 5.3 |
| OKC1873 | 6.0 | 6.7 | 6.0 | 7.3 | 5.7 | 5.0 |
| MSB-1042 | 4.7 | 7.0 | 6.7 | 7.0 | 5.3 | 6.3 |
| *Astro | 6.0 | 6.0 | 6.0 | 5.7 | 4.3 | 6.0 |

TABLE 7-continued

Genetic color of 22 vegetative bermudagrass entries evaluated in the NTEP trial. (9 = dark green; 1 = light green).

| | | | | | | |
|---|---|---|---|---|---|---|
| JSC 77V | 4.3 | 7.0 | 6.7 | 7.0 | 5.7 | 4.7 |
| JSC 80V | 4.3 | 6.0 | 6.0 | 6.3 | 5.3 | 6.0 |
| OKC1406 | 3.7 | 5.3 | 6.0 | 7.3 | 4.7 | 7.3 |
| OKC1666 | 4.7 | 6.0 | 5.7 | 6.3 | 4.3 | 6.0 |
| LSD (0.05) | 1.9 | 1.5 | 1.3 | 1.4 | 1.0 | 1.5 |
| C.V. (%) | 21.0 | 14.1 | 11.2 | 11.4 | 9.1 | 17.9 |

| Entry | MS1 | NM1 | OK1 | TN1 | Mean |
|---|---|---|---|---|---|
| MSB-1026 | 6.0 | 8.0 | 7.0 | 5.7 | 7.0 |
| FB 1628 | 6.3 | 7.3 | 7.3 | 5.0 | 7.0 |
| FB 1902 | 5.0 | 7.7 | 6.3 | 5.7 | 6.9 |
| *Tifway | 6.3 | 7.3 | 6.3 | 6.7 | 6.7 |
| FB 1903 | 6.0 | 6.7 | 6.3 | 6.7 | 6.6 |
| MSB-1017 | 6.0 | 7.0 | 6.7 | 3.7 | 6.6 |
| MSB-1050 | 6.3 | 7.0 | 7.0 | 3.7 | 6.4 |
| OKC1876 | 5.7 | 6.7 | 6.7 | 3.3 | 6.4 |
| MSB-1075 | 6.3 | 7.0 | 6.0 | 4.0 | 6.3 |
| OKC1682 | 6.0 | 6.3 | 6.3 | 5.0 | 6.2 |
| FB 1630 | 5.7 | 6.0 | 6.3 | 5.0 | 6.2 |
| *Tahoma 31 | 6.3 | 5.7 | 6.0 | 4.3 | 6.2 |
| MSB-1048 | 5.7 | 7.7 | 5.0 | 3.0 | 6.1 |
| *Latitude 36 | 6.3 | 6.0 | 6.0 | 3.3 | 6.1 |
| *Tiftuf | 6.0 | 6.0 | 6.3 | 5.0 | 6.0 |
| OKC1873 | 5.7 | 6.0 | 6.0 | 4.3 | 5.9 |
| MSB-1042 | 5.3 | 5.0 | 6.0 | 4.7 | 5.8 |
| *Astro | 5.7 | 8.0 | 5.3 | 4.0 | 5.7 |
| JSC 77V | 5.7 | 5.0 | 6.0 | 4.3 | 5.6 |
| JSC 80V | 6.0 | 4.7 | 5.3 | 5.3 | 5.5 |
| OKC1406 | 6.0 | 6.0 | 5.0 | 3.3 | 5.5 |
| OKC1666 | 5.3 | 5.7 | 5.3 | 3.3 | 5.3 |
| LSD (0.05) | 0.9 | 2.1 | 1.0 | 3.2 | 1.1 |
| C.V. (%) | 9.3 | 19.8 | 9.9 | 44.0 | 17.1 |

Fall color retention rating is typically used to assess the ability of a grass to hold color during the changing climatic conditions of fall, including chilling, frost, and shorter days and daylength hours. NTEP trial revealed that 'MSB-1017' had a fall color retention rating of 6.0 across seven locations, making it ranking in the top statistical group (Table 8). In Missouri (MO1) fall color retention of 'MSB-1017' was higher than 'Latitude 36', 'Tahoma 31' and 'Tifway', but lower than 'TifTuf' and three experimental entries ('MSB-1042', 'OKC1666' and 'OKC1876'—U.S. Plant Pat. No. 35,548).

TABLE 8

Fall color retention ratings of 22 vegetative bermudagrass entries evaluated in the 2019 NTEP trial. (9 = fully green; 1 = brown).

| Entry | AL1 | AR1 | IN1 | MO1 | NM1 | OK1 | VAI | Mean |
|---|---|---|---|---|---|---|---|---|
| FB 1628 | 7.7 | 6.3 | 7.7 | 5.3 | 7.0 | 6.7 | 3.3 | 6.3 |
| FB 1902 | 8.0 | 5.7 | 6.3 | 7.3 | 6.7 | 6.3 | 3.3 | 6.2 |
| OKC1876 | 6.0 | 6.7 | 6.7 | 8.3 | 6.0 | 7.0 | 2.7 | 6.2 |
| MSB-1017 | 8.0 | 5.3 | 6.3 | 6.3 | 6.7 | 7.0 | 2.0 | 6.0 |
| FB 1630 | 5.7 | 6.0 | 7.7 | 4.3 | 6.7 | 7.0 | 3.7 | 5.9 |
| OKC1873 | 6.3 | 7.0 | 6.7 | 5.0 | 5.0 | 7.0 | 3.3 | 5.8 |
| *Tiftuf | 4.7 | 6.3 | 7.7 | 8.0 | 3.0 | 6.7 | 4.0 | 5.8 |
| *Tifway | 5.7 | 4.3 | 7.3 | 3.7 | 6.3 | 7.0 | 5.0 | 5.6 |
| MSB-1075 | 5.0 | 4.3 | 6.0 | 6.0 | 6.3 | 6.7 | 3.7 | 5.4 |
| MSB-1026 | 7.7 | 5.7 | 6.7 | 2.3 | 4.7 | 6.3 | 3.0 | 5.2 |
| MSB-1042 | 3.7 | 4.7 | 6.7 | 8.3 | 4.0 | 6.3 | 2.7 | 5.2 |
| *Astro | 3.3 | 5.0 | 6.3 | 5.3 | 7.0 | 5.3 | 3.0 | 5.0 |
| FB 1903 | 2.7 | 6.0 | 6.0 | 6.0 | 7.0 | 6.0 | 1.0 | 5.0 |
| *Latitude 36 | 5.0 | 5.3 | 7.0 | 2.7 | 6.0 | 6.7 | 2.0 | 5.0 |
| MSB-1050 | 3.0 | 5.3 | 5.7 | 6.7 | 5.0 | 7.0 | 1.0 | 4.8 |
| OKC1666 | 2.7 | 4.3 | 6.7 | 8.3 | 3.3 | 5.7 | 2.3 | 4.8 |
| OKC1682 | 2.7 | 4.7 | 6.7 | 6.3 | 4.0 | 6.0 | 3.0 | 4.8 |
| JSC 77V | 3.3 | 5.7 | 7.3 | 5.3 | 2.7 | 5.7 | 2.7 | 4.7 |

TABLE 8-continued

Fall color retention ratings of 22 vegetative bermudagrass entries evaluated in the 2019 NTEP trial. (9 = fully green; 1 = brown).

| Entry | AL1 | AR1 | IN1 | MO1 | NM1 | OK1 | VAI | Mean |
|---|---|---|---|---|---|---|---|---|
| *Tahoma 31 | 2.7 | 4.7 | 6.7 | 4.3 | 5.0 | 5.7 | 1.7 | 4.4 |
| MSB-1048 | 2.0 | 4.0 | 6.3 | 6.0 | 6.0 | 4.0 | 1.3 | 4.2 |
| JSC 80V | 2.3 | 4.0 | 5.7 | 5.7 | 3.0 | 5.0 | 1.7 | 3.9 |
| OKC1406 | 2.0 | 3.3 | 4.7 | 3.0 | 4.0 | 5.0 | 3.0 | 3.6 |
| LSD (0.05) | 2.1 | 1.6 | 1.1 | 1.6 | 2.8 | 1.3 | 1.6 | 1.8 |
| C.V. (%) | 28.4 | 18.9 | 10.4 | 17.4 | 32.7 | 12.7 | 37.9 | 21.6 |

*Standard entries

Seedhead production is an undesirable trait in turfgrasses. It is evaluated based on a 1-9 scale with 9 being no seedheads. NTEP trial indicated that 'MSB-1017' ranked 2nd with a mean of 8.3 in seedhead rating, and it was ranked significantly higher than two commercial standards 'Latitude 36' and 'Tahoma 31' (Table 9). In 2019 NTEP trial seedhead production of 'MSB-1017' varied across locations. Mean seedhead production of 'MSB-1017' was 8.3 ($LSD_{0.05}$=2.6) and was lower than 'Astro', Latitude 36' and 'Tahoma 31', similarly to seedhead production in Mississippi (MS1). In Indiana (IN1) seedhead production of 'MSB-1017'was lower also than 'Tiftuf'. In Kansas (KS2) it was lower than all standard entries, as well as 'FB1628', 'OKC1666' and 'OKC1876'.

TABLE 9

Seedhead ratings of 22 vegetative bermudagrass entries evaluated in the 2019 NTEP trial. (9 = no seedheads; 1 = maximum seedheads)

| Entry | IN1 | KS2 | MS1 | VA1 | Mean |
|---|---|---|---|---|---|
| MSB-1050 | 9.0 | 8.7 | 9.0 | 7.0 | 8.4 |
| MSB-1017 | 8.7 | 8.3 | 8.7 | 7.3 | 8.3 |
| MSB-1026 | 8.0 | 7.7 | 9.0 | 7.0 | 7.9 |
| OKC1873 | 9.0 | 7.3 | 9.0 | 4.7 | 7.5 |
| MSB-1048 | 8.3 | 6.7 | 8.3 | 5.3 | 7.2 |
| OKC1666 | 8.7 | 4.3 | 8.0 | 7.7 | 7.2 |
| MSB-1075 | 7.3 | 7.0 | 9.0 | 5.3 | 7.2 |
| OKC1876 | 9.0 | 5.7 | 8.3 | 5.3 | 7.1 |
| MSB-1042 | 9.0 | 6.7 | 6.3 | 5.3 | 6.8 |
| FB 1628 | 8.7 | 5.3 | 9.0 | 4.0 | 6.8 |
| FB 1903 | 8.7 | 6.7 | 6.3 | 5.3 | 6.8 |
| OKC1682 | 7.7 | 6.7 | 7.3 | 4.3 | 6.5 |
| *Tifway | 8.3 | 6.0 | 6.3 | 5.3 | 6.5 |
| *Tiftuf | 6.0 | 5.0 | 8.3 | 5.3 | 6.2 |
| *Latitude 36 | 8.3 | 6.3 | 3.0 | 4.3 | 5.5 |
| OKC1406 | 3.3 | 5.3 | 3.7 | 8.7 | 5.3 |
| *Astro | 5.0 | 5.7 | 2.0 | 8.0 | 5.2 |
| FB 1630 | 7.7 | 4.3 | 3.0 | 5.3 | 5.1 |
| FB 1902 | 9.0 | 3.0 | 2.0 | 4.7 | 4.7 |
| *Tahoma 31 | 6.3 | 6.0 | 2.0 | 4.3 | 4.7 |
| JSC 77V | 3.0 | 5.7 | 4.7 | 4.0 | 4.3 |
| JSC 80V | 3.7 | 6.0 | 2.0 | 5.3 | 4.3 |
| LSD (0.05) | 2.1 | 1.6 | 3.1 | 4.6 | 2.6 |
| C.V. (%) | 17.6 | 16.5 | 31.1 | 51.1 | 30.3 |

*Standard entries

In MSU 2016 trial, 'MSB-1017' also performed well in the top statistical group with a mean rating of 8.5, which was ranked significantly higher than 'Riley's Super Sport' (Table 10).

TABLE 10

Seedhead rating of experimental bermudagrass genotypes planted at Mississippi State University in 2016 and evaluated over two growing seasons. (9 = no seedheads; 1 = maximum seedheads).

| Entry | 2017 | 2018 | Mean |
|---|---|---|---|
| MSB-1026 | 9.0 | 9.0 | 9.0 |
| MSB-1006 | 8.9 | 9.0 | 8.9 |
| MSB-1012 | 8.9 | 8.4 | 8.6 |
| MSB-1017 | 8.4 | 8.6 | 8.5 |
| *Tifway | 8.2 | 8.5 | 8.4 |
| MSB-1011 | 8.0 | 8.3 | 8.2 |
| MSB-1003 | 8.3 | 7.9 | 8.1 |
| MSB-1004 | 8.1 | 7.9 | 8.0 |
| MSB-1033 | 8.5 | 7.6 | 8.0 |
| MSB-1010 | 8.0 | 8.1 | 8.0 |
| MSB-1013 | 8.0 | 7.8 | 7.9 |
| MSB-1005 | 7.7 | 8.1 | 7.9 |
| MSB-1022 | 7.9 | 7.9 | 7.9 |
| MSB-1028 | 7.5 | 7.7 | 7.6 |
| MSB-1015 | 7.5 | 7.6 | 7.5 |
| MSB-1020 | 7.6 | 7.3 | 7.5 |
| MSB-1021 | 7.2 | 7.4 | 7.3 |
| MSB-1027 | 7.3 | 7.2 | 7.3 |
| MSB-1018 | 7.2 | 7.2 | 7.2 |
| MSB-1001 | 7.0 | 7.2 | 7.1 |
| MSB-1016 | 7.1 | 6.5 | 6.8 |
| MSB-1014 | 6.5 | 7.1 | 6.8 |
| MSB-1032 | 6.4 | 7.0 | 6.7 |
| *'Riley's Super Sport' | 6.4 | 6.8 | 6.6 |
| MSB-1019 | 6.8 | 6.4 | 6.6 |
| MSB-1031 | 6.5 | 6.7 | 6.6 |
| MSB-1024 | 6.8 | 6.2 | 6.5 |
| MSB-1008 | 6.1 | 6.6 | 6.4 |
| MSB-1007 | 6.3 | 6.3 | 6.3 |
| MSB-1002 | 6.2 | 6.4 | 6.3 |
| MSB-1009 | 6.3 | 6.3 | 6.3 |
| MSB-1029 | 5.5 | 6.0 | 5.8 |
| MSB-1025 | 5.6 | 5.0 | 5.3 |
| LSD (0.05) | 0.4 | 0.4 | 0.3 |
| C.V. (%) | 3.7 | 3.6 | 3.7 |

*Standard entries

Percentage of establishment reflects the relative speed of grass to develop into a mature sod. It is evaluated based on percentage coverage basis, with 100 being maximum establishment and 0 being minimal/no establishment. The NTEP trial revealed that 'MSB-1017' had the 2nd highest percentage of establishment among 22 entries (Table 11). This indicates that 'MSB-1017' is very fast in establishment, which is a preferred trait in turfgrass.

TABLE 11

Percentage of establishment of 22 vegetative bermudagrass entries evaluated in the 2019 NTEP trial. (100 = fast establishment; 0 = slow/no establishment)

| Entry | AL1 | MO1 | FL3 | NM1 | MS1 | KS2 | Mean |
|---|---|---|---|---|---|---|---|
| MSB-1050 | 90.0 | 86.3 | 97.7 | 74.6 | 80.7 | 62.6 | 82.0 |
| MSB-1017 | 76.7 | 81.7 | 99.0 | 72.5 | 71.3 | 72.3 | 78.9 |
| OKC1876 | 56.7 | 90.0 | 94.5 | 78.2 | 69.9 | 57.8 | 74.5 |
| *Tiftuf | 63.3 | 75.0 | 95.4 | 74.5 | 73.3 | 55.0 | 72.8 |
| MSB-1042 | 70.0 | 63.3 | 96.8 | 57.7 | 73.3 | 65.8 | 71.2 |
| MSB-1048 | 73.3 | 61.7 | 93.1 | 59.7 | 72.8 | 61.0 | 70.3 |
| *Astro | 60.0 | 80.0 | 95.5 | 65.6 | 67.5 | 51.7 | 70.1 |
| FB 1628 | 60.0 | 76.7 | 87.1 | 76.3 | 70.8 | 43.6 | 69.1 |
| FB 1630 | 46.7 | 79.7 | 90.9 | 68.3 | 69.5 | 56.0 | 68.5 |
| *Latitude 36 | 40.0 | 83.3 | 91.8 | 76.0 | 71.2 | 47.7 | 68.3 |
| *Tifway | 50.0 | 81.7 | 82.4 | 77.7 | 67.1 | 51.1 | 68.3 |
| FB 1903 | 53.3 | 86.7 | 77.3 | 84.2 | 66.3 | 41.6 | 68.2 |
| *Tahoma 31 | 60.0 | 71.7 | 85.2 | 72.6 | 65.5 | 51.6 | 67.8 |
| MSB-1026 | 56.7 | 76.7 | 89.9 | 64.1 | 72.8 | 45.1 | 67.6 |
| OKC1873 | 43.3 | 86.7 | 86.5 | 62.5 | 70.8 | 45.0 | 65.8 |

TABLE 11-continued

Percentage of establishment of 22 vegetative bermudagrass entries evaluated in the 2019 NTEP trial. (100 = fast establishment; 0 = slow/no establishment)

| Entry | AL1 | MO1 | FL3 | NM1 | MS1 | KS2 | Mean |
|---|---|---|---|---|---|---|---|
| JSC 80V | 26.7 | 88.3 | 90.6 | 68.6 | 65.5 | 49.7 | 64.9 |
| JSC 77V | 46.7 | 65.0 | 95.0 | 73.1 | 69.5 | 38.6 | 64.7 |
| OKC1406 | 20.0 | 86.7 | 91.2 | 55.7 | 65.8 | 51.0 | 61.7 |
| OKC1666 | 30.0 | 80.0 | 73.1 | 58.3 | 67.5 | 56.7 | 60.9 |
| FB 1902 | 35.0 | 68.3 | 73.0 | 69.7 | 68.8 | 48.8 | 60.6 |
| MSB-1075 | 26.7 | 80.0 | 81.9 | 52.9 | 68.8 | 49.1 | 59.9 |
| OKC1682 | 11.7 | 73.3 | 66.0 | 54.9 | 65.5 | 35.3 | 51.1 |
| LSD (0.05) | 27.4 | 25.5 | 6.2 | 17.5 | 6.1 | 9.7 | 20.0 |
| C.V. (%) | 34.2 | 20.3 | 4.7 | 13.5 | 4.9 | 11.7 | 9.8 |

*Standard entries

Percent living ground cover is based on surface area covered by the originally planted species. It is generally used to express damage caused by disease, insects, weed encroachment, or environmental stress. Percent living ground cover was evaluated in spring, summer, and fall depending on individual locations in the NTEP trial (Tables 12).

TABLE 12

Spring percent living ground cover ratings of 22 vegetative bermudagrass entries evaluated in the 2019 NTEP trial. (100 = maximum ground cover; 0 = dead plant or no ground cover)

| Entry | AL1 | AR1 | KS2 | MO1 | MS1 |
|---|---|---|---|---|---|
| *Tiftuf | 93.0 | 95.0 | 70.0 | 90.3 | 99.0 |
| MSB-1017 | 96.0 | 66.7 | 80.0 | 94.3 | 99.0 |
| OKC1876 | 89.7 | 83.3 | 76.7 | 90.0 | 99.0 |
| *Tahoma 31 | 99.0 | 95.0 | 60.0 | 99.0 | 99.0 |
| MSB-1042 | 92.7 | 81.7 | 81.7 | 96.0 | 99.0 |
| *Latitude 36 | 76.3 | 90.0 | 66.7 | 97.7 | 99.0 |
| *Astro | 99.0 | 80.0 | 53.3 | 93.3 | 99.0 |
| FB 1628 | 99.0 | 90.0 | 56.7 | 93.0 | 99.0 |
| *Tifway | 89.3 | 81.7 | 68.3 | 90.0 | 99.0 |
| MSB-1048 | 93.0 | 63.3 | 76.7 | 91.7 | 99.0 |
| MSB-1026 | 86.3 | 78.3 | 61.7 | 85.0 | 99.0 |
| OKC1873 | 80.0 | 93.3 | 61.7 | 88.3 | 99.0 |
| FB 1630 | 92.7 | 88.3 | 48.3 | 94.3 | 99.0 |
| OKC1406 | 56.7 | 86.7 | 75.0 | 91.7 | 99.0 |
| OKC1666 | 63.3 | 85.0 | 76.7 | 80.0 | 99.0 |
| MSB-1050 | 96.0 | 53.3 | 36.7 | 97.0 | 99.0 |
| JSC 77V | 96.0 | 86.7 | 38.3 | 88.0 | 93.0 |
| FB 1902 | 89.3 | 83.3 | 45.0 | 80.0 | 96.0 |
| JSC 80V | 60.0 | 81.7 | 58.3 | 80.0 | 99.0 |
| OKC1682 | 43.3 | 80.0 | 75.0 | 85.0 | 99.0 |
| FB 1903 | 86.3 | 85.0 | 31.7 | 68.3 | 96.0 |
| MSB-1075 | 73.3 | 63.3 | 36.7 | 73.3 | 99.0 |
| LSD (0.05) | 20.0 | 10.8 | 22.9 | 10.9 | 3.1 |
| C.V. (%) | 14.8 | 8.2 | 23.5 | 7.7 | 1.9 |

| Entry | NM1 | TN1 | VA1 | Mean |
|---|---|---|---|---|
| *Tiftuf | 91.7 | 99.0 | 78.3 | 89.5 |
| MSB-1017 | 97.3 | 98.0 | 78.3 | 88.7 |
| OKC1876 | 93.7 | 98.0 | 73.3 | 88.0 |
| *Tahoma 31 | 84.3 | 96.7 | 63.3 | 87.0 |
| MSB-1042 | 69.0 | 94.0 | 78.3 | 86.5 |
| *Latitude 36 | 88.7 | 98.0 | 75.0 | 86.4 |
| *Astro | 90.7 | 98.0 | 76.7 | 86.3 |
| FB 1628 | 84.0 | 98.0 | 65.0 | 85.6 |
| *Tifway | 94.0 | 99.0 | 53.3 | 84.3 |
| MSB-1048 | 80.3 | 98.0 | 65.0 | 83.4 |
| MSB-1026 | 94.0 | 98.3 | 63.3 | 83.3 |
| OKC1873 | 92.0 | 98.7 | 51.7 | 83.1 |
| FB 1630 | 77.0 | 98.7 | 60.0 | 82.3 |
| OKC1406 | 72.7 | 98.3 | 53.3 | 79.2 |
| OKC1666 | 67.0 | 98.0 | 60.0 | 78.6 |

TABLE 12-continued

Spring percent living ground cover ratings of 22 vegetative bermudagrass entries evaluated in the 2019 NTEP trial. (100 = maximum ground cover; 0 = dead plant or no ground cover)

| | | | | |
|---|---|---|---|---|
| MSB-1050 | 96.7 | 97.7 | 48.3 | 78.1 |
| JSC 77V | 70.0 | 97.7 | 46.7 | 77.0 |
| FB 1902 | 87.7 | 97.0 | 35.0 | 76.7 |
| JSC 80V | 70.0 | 97.7 | 63.3 | 76.3 |
| OKC1682 | 87.7 | 99.0 | 26.7 | 74.5 |
| FB 1903 | 81.3 | 97.7 | 33.3 | 72.5 |
| MSB-1075 | 84.3 | 95.0 | 21.7 | 68.3 |
| LSD (0.05) | 17.6 | 2.8 | 16.9 | 18.2 |
| C.V. (%) | 13.0 | 1.8 | 18.2 | 11.3 |

Across eight locations where percent living ground cover data were collected in spring, 'MSB-1017' had the 2nd highest mean rating of 88.7, slightly lower than 'Tiftuf' with an average rating of 89.5 (Table 13). 'MSB-1017' had the highest rating of 97.4 in summer, and 3rd highest rating of 84.2 in fall (Table 13).

TABLE 13

Summer and fall percent living ground cover ratings of 22 vegetative bermudagrass entries in the 2019 NTEP trial.

| | Summer | | | | Fall |
|---|---|---|---|---|---|
| Entry | KS2 | NM1 | TN1 | Mean | AR1 |
| MSB-1017 | 99.0 | 98.7 | 94.7 | 97.4 | 71.7 |
| *Tifway | 94.0 | 98.7 | 97.3 | 96.7 | 75.0 |
| FB 1628 | 96.3 | 97.3 | 96.0 | 96.6 | 45.0 |
| FB 1902 | 95.7 | 98.7 | 95.0 | 96.4 | 53.3 |
| OKC1682 | 97.0 | 96.7 | 95.0 | 96.2 | 16.7 |
| OKC1406 | 97.7 | 96.3 | 94.0 | 96.0 | 46.7 |
| *Tiftuf | 96.3 | 97.7 | 93.0 | 95.7 | 80.0 |
| FB 1630 | 93.7 | 97.0 | 96.3 | 95.7 | 55.0 |
| OKC1876 | 94.7 | 97.3 | 94.3 | 95.4 | 71.7 |
| MSB-1048 | 98.3 | 98.0 | 89.3 | 95.2 | 80.0 |
| MSB-1026 | 93.3 | 96.7 | 95.3 | 95.1 | 51.7 |
| *Astro | 94.0 | 98.3 | 91.3 | 94.6 | 66.7 |
| JSC 80V | 92.3 | 96.3 | 95.0 | 94.6 | 25.0 |
| OKC1873 | 88.3 | 97.3 | 95.3 | 93.7 | 70.0 |
| *Tahoma 31 | 88.3 | 97.0 | 94.3 | 93.2 | 51.7 |
| OKC1666 | 90.7 | 93.3 | 94.3 | 92.8 | 26.7 |
| MSB-1050 | 94.3 | 96.7 | 86.3 | 92.4 | 68.3 |
| FB 1903 | 81.7 | 96.3 | 97.3 | 91.8 | 58.3 |
| MSB-1042 | 97.7 | 78.7 | 96.3 | 90.9 | 75.0 |
| *Latitude 36 | 87.3 | 90.7 | 89.0 | 89.0 | 30.0 |
| MSB-1075 | 80.0 | 93.7 | 88.3 | 87.3 | 26.7 |
| JSC 77V | 80.0 | 89.0 | 91.7 | 86.9 | 61.7 |
| LSD (0.05) | 8.7 | 8.2 | 7.2 | 7.3 | 23.0 |
| C.V. (%) | 5.8 | 5.4 | 4.8 | 5.3 | 26.1 |

| | Fall | | | | |
|---|---|---|---|---|---|
| Entry | KS2 | NM1 | TN1 | VA1 | Mean |
| MSB-1017 | 94.3 | 76.3 | 79.7 | 99.0 | 84.2 |
| *Tifway | 93.0 | 65.7 | 95.0 | 99.0 | 85.5 |
| FB 1628 | 88.0 | 89.3 | 85.7 | 99.0 | 81.4 |
| FB 1902 | 86.3 | 73.7 | 76.7 | 99.0 | 77.8 |
| OKC1682 | 81.7 | 45.3 | 79.0 | 99.0 | 64.3 |
| OKC1406 | 85.0 | 44.0 | 82.3 | 99.0 | 71.4 |
| *Tiftuf | 93.0 | 23.0 | 85.7 | 99.0 | 76.1 |
| FB 1630 | 88.3 | 87.7 | 81.0 | 96.0 | 81.6 |
| OKC1876 | 91.3 | 70.7 | 82.3 | 99.0 | 83.0 |
| MSB-1048 | 96.0 | 77.7 | 79.0 | 99.0 | 86.3 |
| MSB-1026 | 88.0 | 52.3 | 89.3 | 99.0 | 76.1 |
| *Astro | 81.7 | 80.7 | 81.0 | 99.0 | 81.8 |
| JSC 80V | 77.3 | 31.0 | 69.3 | 99.0 | 60.3 |
| OKC1873 | 80.0 | 52.0 | 78.7 | 99.0 | 75.9 |
| *Tahoma 31 | 83.0 | 55.0 | 84.3 | 99.0 | 74.6 |
| OKC1666 | 75.0 | 28.7 | 83.0 | 99.0 | 62.5 |
| MSB-1050 | 78.3 | 50.7 | 77.0 | 99.0 | 74.7 |

TABLE 13-continued

Summer and fall percent living ground cover ratings of 22 vegetative bermudagrass entries in the 2019 NTEP trial.

| | | | | | |
|---|---|---|---|---|---|
| FB 1903 | 73.3 | 91.0 | 77.7 | 99.0 | 79.9 |
| MSB-1042 | 90.0 | 41.7 | 87.7 | 99.0 | 78.7 |
| *Latitude 36 | 68.3 | 44.0 | 80.0 | 99.0 | 64.3 |
| MSB-1075 | 73.3 | 58.7 | 79.3 | 99.0 | 67.4 |
| JSC 77V | 71.7 | 12.0 | 84.7 | 99.0 | 65.8 |
| LSD (0.05) | 16.3 | 44.5 | 19.9 | 1.8 | 28.5 |
| C.V. (%) | 12.1 | 48.6 | 15.1 | 1.1 | 20.8 |

Turfgrass density is a visual estimate of living plants or tillers per unit area. A visual rating of 1-9 is used with 9 equaling maximum density. In the NTEP trial, density ratings were performed at two to four locations in spring, summer, and fall (Table 14). 'MSB-1017' had an average of 5.7, 6.3, and 4.9 in summer, spring, and fall, respectively (Table 14). Although 'MSB-1017' was not highly ranked in density ratings, the least significant different tests indicated that it was not significantly different from the top ratings (Table 14). Density in 2019 NTEP trial depended on location and season (Table 14). In Oklahoma (OK1) spring density of 'MSB-1017' was lower only than 'MSB-1050' and higher than 'Astro', 'Latitude 36' and 'Tifway'. In Tennessee (TN1) spring density of 'MSB-1017' was lower than 'Latitude 36' and 'Tahoma 31', as well as seven experimental entries, including 'OKC 1876'. Density in 2019 NTEP trial depended on location and season. In Oklahoma (OK1) spring density of 'MSB-1017' was lower only than 'MSB-1050' and higher than 'Astro', 'Latitude 36' and 'Tifway'. In Tennessee (TN1) spring density of 'MSB-1017' was lower than 'Latitude 36' and 'Tahoma 31', as well as seven experimental entries, including 'OKC 1876'.

TABLE 14

Density ratings of 22 vegetative bermudagrass entries in the 2019 NTEP trial. (9 = very high; 1 = low).

| | Spring Density | | | Summer Density | | |
|---|---|---|---|---|---|---|
| Entry | OK1 | TN1 | Mean | IN1 | MS1 | OK1 |
| MSB-1026 | 7.0 | 8.0 | 7.5 | 8.3 | 6.3 | 7.0 |
| JSC 80V | 6.3 | 8.3 | 7.3 | 7.3 | 6.7 | 6.7 |
| OKC1406 | 6.0 | 8.0 | 7.0 | 7.7 | 5.7 | 6.3 |
| OKC1876 | 7.0 | 6.7 | 6.8 | 8.0 | 7.0 | 7.0 |
| OKC1666 | 6.0 | 7.0 | 6.5 | 6.7 | 6.7 | 6.0 |
| OKC1873 | 6.7 | 6.3 | 6.5 | 7.0 | 5.7 | 7.0 |
| *Tahoma 31 | 6.7 | 6.0 | 6.3 | 7.3 | 6.3 | 7.0 |
| *Latitude 36 | 6.3 | 5.7 | 6.0 | 7.7 | 5.7 | 7.0 |
| MSB-1050 | 8.0 | 4.0 | 6.0 | 8.3 | 7.3 | 8.0 |
| JSC 77V | 6.0 | 6.0 | 6.0 | 7.3 | 6.7 | 6.3 |
| MSB-1042 | 6.3 | 5.3 | 5.8 | 7.7 | 7.0 | 7.0 |
| FB 1628 | 7.0 | 4.7 | 5.8 | 7.7 | 6.0 | 7.0 |
| OKC1682 | 6.0 | 5.3 | 5.7 | 7.3 | 6.3 | 6.7 |
| MSB-1017 | 7.0 | 4.3 | 5.7 | 7.3 | 7.0 | 7.0 |
| MSB-1075 | 7.3 | 4.0 | 5.7 | 6.3 | 6.3 | 8.0 |
| MSB-1048 | 6.0 | 5.0 | 5.5 | 7.3 | 6.0 | 7.7 |
| FB 1902 | 5.7 | 5.3 | 5.5 | 7.0 | 6.0 | 6.0 |
| *Tiftuf | 6.7 | 4.0 | 5.3 | 7.7 | 7.0 | 7.0 |
| *Astro | 5.7 | 5.0 | 5.3 | 5.7 | 6.0 | 6.0 |
| FB 1903 | 5.3 | 5.0 | 5.2 | 7.0 | 6.0 | 6.7 |
| FB 1630 | 6.0 | 4.3 | 5.2 | 6.0 | 6.0 | 6.0 |
| *Tifway | 6.0 | 4.0 | 5.0 | 8.0 | 6.0 | 7.0 |
| LSD (0.05) | 0.6 | 1.4 | 2.6 | 1.1 | 0.7 | 0.6 |
| C.V. (%) | 6.1 | 16.0 | 11.5 | 9.4 | 7.3 | 5.4 |

TABLE 14-continued

Density ratings of 22 vegetative bermudagrass entries in the 2019 NTEP trial. (9 = very high; 1 = low).

| | Summer Density | | Fall Density | | |
|---|---|---|---|---|---|
| Entry | TN1 | Mean | OK1 | TN1 | Mean |
| MSB-1026 | 6.7 | 7.1 | 6.7 | 6.3 | 6.5 |
| JSC 80V | 4.7 | 6.3 | 6.3 | 2.3 | 4.3 |
| OKC1406 | 4.0 | 5.9 | 7.0 | 3.3 | 5.2 |
| OKC1876 | 4.0 | 6.5 | 7.0 | 2.3 | 4.7 |
| OKC1666 | 5.7 | 6.3 | 5.0 | 6.7 | 5.9 |
| OKC1873 | 4.7 | 6.1 | 7.0 | 2.7 | 4.9 |
| *Tahoma 31 | 5.3 | 6.5 | 6.3 | 4.7 | 5.5 |
| *Latitude 36 | 5.7 | 6.5 | 7.0 | 6.7 | 6.9 |
| MSB-1050 | 5.3 | 7.3 | 8.0 | 4.0 | 6.0 |
| JSC 77V | 5.7 | 6.5 | 6.3 | 4.3 | 5.3 |
| MSB-1042 | 5.7 | 6.8 | 7.3 | 6.0 | 6.7 |
| FB 1628 | 6.0 | 6.7 | 6.7 | 5.7 | 6.2 |
| OKC1682 | 6.3 | 6.7 | 6.7 | 7.0 | 6.9 |
| MSB-1017 | 4.0 | 6.3 | 6.7 | 3.0 | 4.9 |
| MSB-1075 | 4.7 | 6.3 | 7.0 | 3.7 | 5.4 |
| MSB-1048 | 6.0 | 6.8 | 6.3 | 5.7 | 6.0 |
| FB 1902 | 7.3 | 6.6 | 6.3 | 5.7 | 6.0 |
| *Tiftuf | 6.3 | 7.0 | 6.7 | 6.3 | 6.5 |
| *Astro | 5.0 | 5.7 | 5.7 | 6.0 | 5.9 |
| FB 1903 | 7.3 | 6.8 | 6.3 | 7.3 | 6.8 |
| FB 1630 | 5.7 | 5.9 | 6.0 | 4.3 | 5.2 |
| *Tifway | 6.0 | 6.8 | 7.0 | 6.0 | 6.5 |
| LSD (0.05) | 3.0 | 1.4 | 0.9 | 2.9 | 3.6 |
| C.V. (%) | 33.3 | 15.8 | 8.1 | 36.5 | 13.3 |

*Standard entries

Spring green-up is a measure of the transition from winter dormancy to active spring growth. It is based on plot color rather than genetic color. The visual rating of spring green-up is based on a 1-9 scale with 1 being straw brown and 9 being dark green. Spring green-up data were collected across nine locations, and 'MSB-1017' had an average rating of 5.0 across nine locations, similar to the mean rating of 'Tifway' (Table 15). This indicates that 'MSB-1017' has similar cold tolerance with 'Tifway', a successful bermudagrass cultivar that has been used for over half a century.

TABLE 15

Spring green-up ratings of 22 vegetative bermudagrass entries evaluated in the 2019 NTEP trial. (9 = dark green; 1 = straw brown).

| Entry | AL1 | AR1 | IN1 | KS2 | KY1 |
|---|---|---|---|---|---|
| *Tahoma 31 | 7.3 | 9.0 | 7.7 | 6.7 | 5.7 |
| *Latitude 36 | 4.0 | 7.7 | 8.7 | 7.7 | 5.3 |
| *Tiftuf | 7.0 | 7.3 | 7.3 | 6.3 | 5.0 |
| FB 1628 | 8.7 | 6.7 | 7.0 | 6.7 | 4.0 |
| *Astro | 7.3 | 5.3 | 8.0 | 4.7 | 4.7 |
| MSB-1026 | 7.0 | 7.3 | 7.3 | 6.0 | 3.7 |
| OKC1666 | 3.0 | 7.0 | 6.7 | 6.3 | 5.7 |
| OKC1876 | 6.0 | 6.7 | 7.3 | 5.3 | 2.7 |
| MSB-1042 | 6.0 | 5.3 | 8.7 | 5.7 | 2.0 |
| OKC1406 | 2.7 | 6.7 | 8.7 | 6.7 | 4.0 |
| FB 1630 | 6.3 | 6.3 | 6.0 | 5.3 | 2.7 |
| JSC 77V | 6.0 | 6.7 | 6.3 | 4.0 | 5.3 |
| *Tifway | 7.0 | 4.7 | 6.0 | 6.3 | 2.7 |
| OKC1873 | 5.3 | 7.0 | 6.3 | 3.7 | 2.7 |
| MSB-1017 | 8.3 | 5.0 | 6.0 | 4.0 | 1.7 |
| JSC 80V | 2.7 | 4.3 | 6.7 | 6.0 | 3.7 |
| OKC1682 | 1.0 | 5.7 | 5.7 | 6.3 | 4.3 |
| FB 1902 | 5.3 | 4.7 | 4.0 | 4.0 | 2.3 |
| FB 1903 | 5.0 | 4.3 | 4.3 | 3.3 | 3.3 |
| MSB-1048 | 6.3 | 2.7 | 5.3 | 3.0 | 1.7 |
| MSB-1050 | 6.7 | 2.7 | 5.7 | 2.0 | 1.0 |
| MSB-1075 | 5.0 | 3.3 | 4.0 | 3.7 | 2.0 |

TABLE 15-continued

Spring green-up ratings of 22 vegetative bermudagrass entries evaluated in the 2019 NTEP trial. (9 = dark green; 1 = straw brown).

| | | | | | |
|---|---|---|---|---|---|
| LSD (0.05) | 2.8 | 2.1 | 2.1 | 1.5 | 1.5 |
| C.V. (%) | 31.3 | 23.2 | 19.9 | 17.5 | 26.4 |
| Entry | MS1 | NM1 | OK1 | VA1 | Mean |
| *Tahoma 31 | 8.3 | 6.7 | 4.7 | 3.7 | 6.6 |
| *Latitude 36 | 8.3 | 7.7 | 3.0 | 5.7 | 6.4 |
| *Tiftuf | 9.0 | 8.0 | 3.3 | 4.7 | 6.4 |
| FB 1628 | 8.7 | 7.7 | 2.7 | 4.0 | 6.2 |
| *Astro | 9.0 | 8.0 | 3.0 | 5.3 | 6.1 |
| MSB-1026 | 7.3 | 8.0 | 3.0 | 4.7 | 6.0 |
| OKC1666 | 8.7 | 6.3 | 4.0 | 6.0 | 6.0 |
| OKC1876 | 8.3 | 8.3 | 1.7 | 6.3 | 5.9 |
| MSB-1042 | 9.0 | 6.3 | 2.0 | 6.0 | 5.7 |
| OKC1406 | 8.7 | 5.7 | 2.7 | 4.3 | 5.6 |
| FB 1630 | 8.3 | 7.3 | 3.7 | 3.7 | 5.5 |
| JSC 77V | 8.7 | 6.0 | 5.0 | 1.3 | 5.5 |
| *Tifway | 9.0 | 8.3 | 2.3 | 3.0 | 5.5 |
| OKC1873 | 5.7 | 7.3 | 3.3 | 4.3 | 5.1 |
| MSB-1017 | 7.0 | 8.0 | 1.3 | 3.7 | 5.0 |
| JSC 80V | 8.0 | 6.7 | 3.0 | 3.0 | 4.9 |
| OKC1682 | 8.0 | 7.0 | 4.0 | 2.0 | 4.9 |
| FB 1902 | 8.0 | 7.7 | 3.7 | 1.7 | 4.6 |
| FB 1903 | 7.3 | 6.0 | 2.3 | 1.7 | 4.2 |
| MSB-1048 | 8.3 | 6.3 | 1.3 | 1.3 | 4.0 |
| MSB-1050 | 8.3 | 8.7 | 0.3 | 1.0 | 4.0 |
| MSB-1075 | 6.0 | 6.7 | 2.0 | 1.3 | 3.8 |
| LSD (0.05) | 1.2 | 1.7 | 1.1 | 3.0 | 2.0 |
| C.V. (%) | 9.3 | 15.1 | 24.2 | 51.3 | 23.1 |

*Standard entries

Disease resistance is important factor in cultivar development. In MSU 2017 home lawn trial, disease resistance rating of experimental lines to leafspot (*Bipolaris cynodontis*) were collected from September 7 to Sep. 25, 2017. Area under disease pressure curve (AUDPC) values were calculated for this period. Encouragingly, 'MSB-1017' ranked in the top among tested entries and was ranked significantly higher than both 'Tifway' and 'Riley's Super Sport' (Table 16).

TABLE 16

Leafspot disease rating, turf quality, leaf texture, and seedhead rating of experimental bermudagrass genotypes planted at Mississippi State University in 2017 under a home lawn management regime. Lower area under disease pressure curve values (AUDPC) indicate higher level of resistance to leafspot (*Bipolaris cynodontis*).

| Entry | AUDPC | Turf quality | Leaf texture | Seedhead |
|---|---|---|---|---|
| MSB-1018 | 38.3 | 5.4 | 7.0 | 6.2 |
| MSB-1016 | 44.7 | 5.6 | 7.0 | 6.4 |
| MSB-1017 | 45.0 | 6.5 | 7.0 | 8.2 |
| MSB-1013 | 51.0 | 6.7 | 7.0 | 7.0 |
| *'Riley's Super Sport' | 59.8 | 5.6 | 5.7 | 6.3 |
| *Tifway | 61.2 | 6.4 | 6.7 | 7.6 |
| MSB-1008 | 63.7 | 5.7 | 6.0 | 5.5 |
| MSB-1022 | 69.7 | 6.4 | 7.0 | 7.6 |
| MSB-1010 | 72.0 | 6.3 | 7.0 | 7.6 |
| MSB-1004 | 74.7 | 5.7 | 7.0 | 7.0 |
| MSB-1026 | 75.0 | 6.0 | 6.0 | 8.9 |
| MSB-1003 | 89.5 | 5.0 | 5.7 | 5.6 |
| MSB-1012 | 105.3 | 6.4 | 6.0 | 7.6 |
| MSB-1006 | 106.5 | 6.4 | 6.0 | 8.9 |
| MSB-1011 | 118.0 | 5.5 | 5.0 | 6.6 |
| LSD (0.05) | 6.8 | 0.4 | 0.5 | 0.5 |
| C.V. (%) | 5.7 | 3.9 | 4.2 | 4.5 |

*Standard entries

In addition, 'MSB-1017' ranked 2nd in turfgrass quality rating (6.5), 1st in leaf texture (7.0), and 3rd in seedhead rating (Table 17). In the 2019 NTEP trial, disease and insect ratings were collected in Indiana using 1-9 scale, with 1 equaling no resistance or 100% injury, and 9 equaling complete resistance or no injury. 'MSB-1017' was the best entry in this trial with a mean rating of 8.0 (Table 17).

TABLE 17

Disease and insect damage evaluated in Indiana in the NTEP trial. Data were collected on a 1 to 9 scale, with 1 equaling no resistance or 100% injury, and 9 equaling complete resistance or no injury.

| Entry | IN1 |
|---|---|
| MSB-1017 | 8.0 |
| MSB-1075 | 8.0 |
| *Astro | 7.3 |
| *Latitude 36 | 7.3 |
| FB 1902 | 7.0 |
| FB 1903 | 7.0 |
| OKC1682 | 7.0 |
| *Tifway | 7.0 |
| FB 1628 | 6.7 |
| MSB-1042 | 6.7 |
| *Tahoma 31 | 6.7 |
| *Tiftuf | 6.7 |
| JSC 77V | 6.3 |
| JSC 80V | 6.3 |
| OKC1406 | 6.3 |
| OKC1873 | 6.0 |
| OKC1876 | 6.0 |
| FB 1630 | 5.7 |
| MSB-1026 | 5.3 |
| MSB-1050 | 5.0 |
| OKC1666 | 5.0 |
| LSD (0.05) | 2.4 |
| C.V. (%) | 19.0 |

*Standard entries

Table 18 below provides a comparison of MSB-1017 with seven other grass varieties. Four pots of each grass were grown in the greenhouse. The longest leaf at the third node below the apical meristem of the stolon and erect shoot was used for the measurement of leaf length (mm) and leaf width (mm) with digital calipers with four replications. Four random stolons and erect shoots on each pot were measured for internode length (mm) and diameter (mm) between the third and fourth fully extended nodes from the apical meristem. All pots grew from plugs harvested from Starkville, Mississippi in May 2023.

TABLE 18

| Cultivar | LLES | LWES | ILES | IDES |
|---|---|---|---|---|
| MSB-1017 | 39.375 | 2.0288 | 13.135 | 0.7656 |
| MSB-1042 | 57.9375 | 1.9738 | 21.9475 | 0.805 |
| MSB-1050 | 27.75 | 1.8956 | 15.3744 | 0.6281 |
| MSB-1080 | 43.8125 | 2.2406 | 14.0244 | 0.7525 |
| 'Riley's Super Sport' | 42 | 2.5837 | 14.9744 | 0.9431 |
| Trans 1 | 33.375 | 1.595 | 16.8512 | 0.4863 |
| TifTuf | 37.125 | 2.1488 | 16.6244 | 0.6975 |
| MSB-04-264 | 41.5 | 1.7944 | 13.1244 | 0.7731 |
| LSD | 6.4167 | 0.151 | 3.1491 | 0.0941 |

| Cultivar | LLS | LWS | ILS | IDS |
|---|---|---|---|---|
| MSB-1017 | 15.125 | 2.025 | 40.1563 | 1.07 |
| MSB-1042 | 33.9375 | 1.9594 | 30.3812 | 0.9112 |
| MSB-1050 | 9.6875 | 2.0513 | 42.7644 | 0.9044 |
| MSB-1080 | 22.6875 | 2.1575 | 12.0138 | 0.9631 |

TABLE 18-continued

| | | | | |
|---|---|---|---|---|
| 'Riley's Super Sport' | 20 | 2.4919 | 36.7106 | 1.24 |
| Trans 1 | 13.9375 | 1.6044 | 15.5356 | 0.8019 |
| TifTuf | 16 | 2.2694 | 25.7831 | 1.0388 |
| MSB-04-264 | 10.6875 | 1.8544 | 32.1012 | 1.185 |
| LSD | 4.4302 | 0.2346 | 5.3547 | 0.1187 |

LLES - leaf length erect shoot; LWES - leaf width erect shoot; ILES - internode length erect shoot; IDES - internode diameter erect shoot; LLS - leaf length stolen; LWS - leaf width stolen; ILS - internode length stolen; and IDS - internode diameter stolen Table 19 below provides a comparison of MSB-1017 with 22 other grass varieties Riverside, California in 2020 under drought conditions. Table 19 shows 'MSB-1017' having a better fall color retention in Riverside, California than 'Tifway', 'Latitude 36' and but lower fall color retention than 'OKC 1876'.

TABLE 19

Turfgrass Quality under drought and other ratings at Riverside, CA (CA3), 2020 (1-9; 9 = best)

| Name | Genetic Color | Leaf Texture | Bermudagrass mite | Fall Color Nov | Turfgrass Quality Jan | Feb | Mar | Apr |
|---|---|---|---|---|---|---|---|---|
| MSB-1017 | 8.3 | 6.7 | 9.0 | 7.7 | 5.3 | 6.0 | 8.7 | 6.7 |
| TIFTUF | 6.7 | 6.7 | 8.7 | 8.0 | 5.7 | 5.7 | 7.7 | 6.0 |
| OKC1873 | 6.3 | 6.3 | 9.0 | 7.7 | 5.7 | 6.0 | 8.7 | 5.7 |
| OKC1876 | 7.3 | 7.0 | 8.3 | 9.0 | 5.7 | 6.0 | 7.7 | 5.7 |
| MSB-1042 | 7.7 | 7.0 | 9.0 | 7.3 | 4.0 | 4.3 | 7.7 | 5.7 |
| OKC1682 | 7.7 | 6.7 | 9.0 | 6.7 | 4.7 | 5.3 | 7.3 | 6.0 |
| FB 1628 | 8.3 | 6.0 | 8.3 | 8.3 | 4.7 | 5.0 | 7.3 | 5.7 |
| MSB-1050 | 9.0 | 8.0 | 8.7 | 8.0 | 4.3 | 4.0 | 8.0 | 5.3 |
| FB 1903 | 8.3 | 5.7 | 9.0 | 7.7 | 3.3 | 3.7 | 6.7 | 3.7 |
| TIFWAY | 6.7 | 6.0 | 9.0 | 6.0 | 4.7 | 4.7 | 7.0 | 5.3 |
| FB 1630 | 7.3 | 5.0 | 8.7 | 7.7 | 4.7 | 5.0 | 7.3 | 4.0 |
| FB 1902 | 7.0 | 5.7 | 9.0 | 8.0 | 4.3 | 4.7 | 7.7 | 4.3 |
| TAHOMA 31 | 8.0 | 6.7 | 8.0 | 4.0 | 4.0 | 4.0 | 7.0 | 5.3 |
| OKC1666 | 5.0 | 6.7 | 8.0 | 6.3 | 4.7 | 4.3 | 6.3 | 5.7 |
| MSB-1026 | 9.0 | 6.3 | 5.7 | 5.7 | 3.7 | 3.7 | 8.3 | 4.3 |
| MSB-1075 | 9.0 | 5.7 | 5.0 | 7.7 | 3.7 | 4.0 | 7.7 | 5.3 |
| JSC 80V | 4.3 | 6.3 | 8.7 | 4.3 | 3.7 | 3.7 | 5.0 | 3.7 |
| LATITUDE 36 | 5.3 | 6.7 | 9.0 | 6.0 | 4.3 | 4.7 | 5.3 | 4.7 |
| MSB-1048 | 8.0 | 7.0 | 9.0 | 4.7 | 3.0 | 3.0 | 6.0 | 4.7 |
| OKC1406 | 6.3 | 6.7 | 8.7 | 4.7 | 3.0 | 3.0 | 7.0 | 4.0 |
| ASTRO | 4.7 | 5.3 | 8.0 | 6.3 | 3.7 | 3.7 | 4.7 | 4.0 |
| JSC 77V | 5.0 | 6.0 | 8.3 | 3.7 | 3.7 | 4.0 | 7.0 | 4.0 |
| LSD VALUE | 1.2 | 0.7 | 1.1 | 1.3 | 0.8 | 0.8 | 1.1 | 0.9 |
| C.V. (%) | 11.1 | 6.9 | 8.5 | 12.7 | 12.5 | 11.7 | 10.1 | 11.4 |

| Name | Turfgrass Quality May | June | July | Aug | Sep | Oct | Nov | Mean |
|---|---|---|---|---|---|---|---|---|
| MSB-1017 | 7.7 | 7.7 | 7.7 | 5.3 | 6.7 | 5.7 | 6.3 | 6.7 |
| TIFTUF | 7.7 | 6.7 | 7.0 | 6.0 | 6.7 | 5.7 | 7.3 | 6.5 |
| OKC1873 | 7.0 | 6.3 | 7.0 | 5.0 | 6.0 | 6.0 | 6.3 | 6.3 |
| OKC1876 | 8.0 | 6.0 | 6.7 | 5.3 | 6.0 | 5.3 | 7.0 | 6.3 |
| MSB-1042 | 7.0 | 7.3 | 7.3 | 5.0 | 5.3 | 6.3 | 6.3 | 6.0 |
| OKC1682 | 7.7 | 7.7 | 7.3 | 5.0 | 5.3 | 4.3 | 4.7 | 5.9 |
| FB 1628 | 6.7 | 6.0 | 6.3 | 5.3 | 5.3 | 5.0 | 6.3 | 5.8 |
| MSB-1050 | 7.0 | 6.3 | 6.7 | 5.7 | 5.7 | 5.3 | 5.3 | 5.8 |
| FB 1903 | 5.7 | 5.7 | 6.3 | 6.7 | 7.3 | 5.0 | 6.0 | 5.5 |
| TIFWAY | 6.0 | 5.7 | 6.7 | 5.3 | 5.3 | 4.7 | 4.7 | 5.5 |
| FB 1630 | 6.0 | 5.7 | 5.7 | 4.7 | 4.7 | 5.0 | 5.7 | 5.3 |
| FB 1902 | 5.7 | 5.0 | 5.0 | 4.3 | 5.7 | 5.3 | 6.7 | 5.3 |
| TAHOMA 31 | 6.0 | 6.3 | 6.3 | 5.3 | 5.0 | 5.0 | 4.0 | 5.3 |
| OKC1666 | 6.7 | 5.7 | 5.0 | 4.3 | 5.3 | 4.0 | 5.3 | 5.2 |

TABLE 19-continued

| Turfgrass Quality under drought and other ratings at Riverside, CA (CA3), 2020 (1-9; 9 = best) | | | | | | | | |
|---|---|---|---|---|---|---|---|---|
| MSB-1026 | 5.7 | 5.7 | 5.3 | 4.7 | 5.3 | 5.0 | 4.0 | 5.1 |
| MSB-1075 | 4.7 | 5.3 | 5.3 | 5.0 | 5.0 | 4.7 | 5.0 | 5.1 |
| JSC 80V | 6.0 | 7.0 | 6.7 | 5.0 | 4.3 | 4.3 | 4.7 | 4.9 |
| LATITUDE 36 | 6.7 | 5.7 | 5.3 | 4.3 | 4.3 | 3.7 | 5.0 | 4.9 |
| MSB-1048 | 6.7 | 7.0 | 5.3 | 5.0 | 5.0 | 3.7 | 4.7 | 4.9 |
| OKC1406 | 6.0 | 5.0 | 6.0 | 4.0 | 4.3 | 4.3 | 4.0 | 4.6 |
| ASTRO | 5.0 | 5.3 | 5.0 | 4.3 | 4.3 | 5.0 | 4.7 | 4.5 |
| JSC 77V | 5.7 | 4.7 | 3.7 | 3.0 | 3.0 | 3.0 | 3.7 | 4.1 |
| LSD VALUE | 0.9 | 0.8 | 0.9 | 0.9 | 0.9 | 1.1 | 1.0 | 0.5 |
| C.V. (%) | 8.6 | 8.7 | 9.7 | 11.1 | 10.5 | 13.4 | 11.7 | 5.7 |

COMPARISON WITH PARENTAL LINES AND KNOWN VARIETY

'MSB-1017' can be distinguished from other bermudagrass cultivars by DNA profiling. FIG. 7 is a pictorial representation of a phylogenetic tree that shows 'MSB-1017' is genetically different from the other bermudagrass cultivars analyzed. Samples were collected from grass cultivars grown in individual pots in a greenhouse. After a few weeks of growth, DNA was extracted from the vegetative tissue. Six SSR markers were amplified from 'MSB-1017', parental lines 'Riley's Super Sport' and 'Trans 1', three other experimental entries that are also progeny of these parents and seven cultivars ('Latitude 36', 'Riviera'—U.S. PVP Certificate No. 009500227, 'TifGrand'—U.S. Plant Pat. No. 21,017, 'Tifgreen'—unpatented, 'TifEagle'—U.S. Plant Pat. No. 11,163, TifTuf' and 'Tifway'). Four markers generated good amplification and polymorphism (shown in Table 19 below). Thirty-four fragments were generated by these markers. Genotyping was performed and analyzed using Dice genetic similarity coefficient. Dendrogram was constructed using Unweighted Pair Group Method with Arithmetic Mean (UPGMA). 'MSB-1017', 'MSB-1042' and 'MSB-1050' clustered together with 'Celebration' and 'Trans 1', indicating they are their progeny. These five entries formed cluster distant from 'MSB-1080' and cultivars.

In addition, morphological characteristics allow to distinguish 'MSB-1017' from its parents. Hairs on adaxial surface of 'Riley's Super Sport' are abundant, while 'Trans 1' has very sparse and short hairs on adaxial surface 'MSB-1017' is intermediate between two parents in leaf hair abundance. Leaf color of 'Trans 1' assessed using Munsell® Color Chart matches 5GY/4/4 for both sides of the leaf blade, and color of leaf sheath matches 5GY/6/6. Both sides of the leaf blade of 'Riley's Super Sport' matched 7.5GY/4/4 and leaf sheath 5GY/6/6. 'MSB-1017' has leaf blade color similar to 'Trans 1' (5GY/3/4; 5GY/4/4), but color of leaf sheath is distinct from both parents (2.5GY/6/4).

TABLE 20

Raw data for simple sequence repeats (SSR) markers analysis

| | Marker | | | |
|---|---|---|---|---|
| Entry | Chase109 | Comp-61826_c0_seq6 | Comp-62584_c0_seq6 | Comp-61529_c0_seq1 |
| Tifgreen | 303.96, 315.81 | 128.77, 130.91, 134.52 | 148.43, 151.62 | 143.01, 149.91, 157.12 |
| TifEagle | 303.95, 315.76 | 128.71, 130.84, 134.52 | 148.44, 151.53 | 143.06, 149.91, 157.09 |
| Trans1 | 309.70, 336.28 | 131.4 | 149.54, 163.15 | 149.82, 152.88 |
| MSB-1017 | 336.22 | 131.43, 134.55 | 149.54, 162.93 | 136.90, 147.69, 152.90 |
| MSB-1042 | 336.26 | 131.7 | 150.51, 160.24, 163.23 | 147.71, 152.88 |
| MSB-1050 | 309.82 | 131.40, 134.50 | 149.45, 163.00 | 139.58, 147.78, 152.88 |
| MSB1080 | 331.51 | 128.68, 131.62 | 116.49 | 136.90, 147.59, 149.82 |
| Riley Super Sport | 207.53 | 131.78, 134.52 | 160.16, 162.91 | 139.57, 147.71 |
| Tifway | 302.25, 329.97, 340.73 | 128.72, 131.53 | 141.80, 166.02 | 147.67, 149.91 |
| DT-1 (TifTuf) | 302.29, 306.98, 333.90 | 128.71, 131.78, 140.04 | 141.75, 151.53 | 149.91 |
| TifGrand | 302.29, 315.54, 330.01, 340.73 | 128.65, 131.57 | 141.77, 151.62 | 147.61, 149.73 |
| Latitude 36 | 331.3 | 134.52 | 148.44, 163.14 | 149.82 |
| Riviera | 192.61 | 134.49 | 148.52, 165.90 | 149.91 |
| Water | 51.17 | 40.55 | 36.02 | 59.25 |

I claim:

1. A new and distinct cultivar of Bermudagrass Plant Named 'MSB-1017' as described and illustrated herein.

* * * * *